(12) United States Patent
Ulvskov et al.

(10) Patent No.: US 6,420,628 B1
(45) Date of Patent: Jul. 16, 2002

(54) SEED SHATTERING

(75) Inventors: Peter Ulvskov, Charlottenlund (DK); Robin Child, Bristol (GB); Henri Van Onckelen, Dourne; Els Prinsen, Kontich, both of (BE); Bernhard Borkhardt, Farum (DK); Lilli Sander, Copenhagen (DK); Morten Petersen, Copenhagen (DK); Gert Bundgard Poulsen, Copenhagen (DK); Johan Botterman, Zevergem (BE)

(73) Assignee: Plant Genetic Systems, N.V., Ghent (BE)

( * ) Notice: Subject to any disclaimer, the term of this patent is extended or adjusted under 35 U.S.C. 154(b) by 0 days.

(21) Appl. No.: 09/051,239

(22) PCT Filed: Oct. 4, 1996

(86) PCT No.: PCT/EP96/04313

§ 371 (c)(1),
(2), (4) Date: Sep. 28, 1998

(87) PCT Pub. No.: WO97/13865

PCT Pub. Date: Apr. 17, 1997

(30) Foreign Application Priority Data

Oct. 6, 1995 (EP) ............................................ 95402241
Dec. 8, 1995 (EP) ............................................ 95203328

(51) Int. Cl.[7] ........................ C12N 15/09; C12N 15/29; C12N 15/82; A01H 5/00
(52) U.S. Cl. ........................ 800/278; 800/290; 800/283; 800/287; 800/298; 800/306; 435/69.1; 435/199; 435/419; 435/468; 536/23.1; 536/24.1; 536/23.6
(58) Field of Search ................................. 800/290, 278, 800/283, 287, 298, 306; 435/69.1, 199, 419, 468; 536/23.1, 24.1, 23.6

(56) References Cited

FOREIGN PATENT DOCUMENTS

| EP | 0271988 A2 | 6/1988 |
|---|---|---|
| WO | WO9302197 | 2/1993 |
| WO | WO9401572 | 1/1994 |
| WO | WO9423043 | 10/1994 |
| WO | WO9630529 | 10/1996 |

OTHER PUBLICATIONS

Petersen et al., *Plant Molecular Biology*, 31: 517–527 (1996) XP002025026.
Bird et al., *Plant Molecular Biology*, 11: 651–662 (1998) XP002002156.
Petersen et al., *Annual Meeting of the American Society of Plant Physiologists, Charlotte, North Carolina, USA, Jul. 29–Aug. 2, 1995. Plant Physiology (Rockville)*, 108 (2 suppl.) (1995) XP002002155, Abstract No. 342.
Sander, L., *EMBL Sequence Database* Rel. 48 Accession No. X98373 (Jun. 1996) XP002025254.
Borkhardt et al., *Annual Meeting of the American Society of Plant Physiologists, Portland, Oregon, USA, Jul. 30–Aug. 3, 1994. Plant Physiology (Rockville)* 105 (1 suppl)., 56 (1994) XP002002157, Abstract No. 261.
Prakash et al., *Genetical Research* vol. 56, No. 1, pp. 1, 2 (Aug. 1, 1990) XP000574919.
Jenkins et al., *Journal of Experimental Botany*, vol. 47 No. 294 pp. 111–115 (Jan. 1, 1996) XP000570275.

Primary Examiner—Phuong T. Bui
Assistant Examiner—Medina A. Ibrahim
(74) Attorney, Agent, or Firm—Birch, Stewart, Kolasch & Birch, LLP.

(57) ABSTRACT

A plant is provided which contains at least one dehiscence zone (DZ)-selective chimeric gene incorporated in the nuclear genome of its cells, wherein said DZ-selective chimeric gene comprises the following operably linked DNA fragments: a) a transcribed DNA region encoding: 1) a RNA which, when produced in cells of a particular DZ of the plant, prevents, inhibits or reduces the expression in DZ cells of an endogenous gene of the plant encoding a cell wall hydrolase, particularly an endopolygalacturonase, or, 2) a protein or polypeptide, which when produced in DZ cells, kills or disables them or interferes with their normal metabolism, physiology or development; b) a plant expressible promoter which directs expression of transcribed DNA region at least in DZ cells, provided that if transcribed DNA region encodes a protein or polypeptide, or encodes an antisense RNA or ribozyme directed to a sense RNA encoded by an endogenous gene that is expressed in plant in cells other than DZ cells, plant expressible promoter is a DZ-selective promoter, which directs expression of transcribed region selectively in DZ cells and wherein plant is characterized by modified dehiscence properties, preferably delayed dehiscence, when compared to a plant not containing DZ-selective chimeric gene.

11 Claims, No Drawings

SEED SHATTERING

This application is the national phase under 35 U.S.C. §371 of prior PCT International Application No. PCT/EP96/04313 which has an International filing date of Oct. 4, 1996, which designated the United States of America, the entire contents of which are hereby incorporated by reference.

INTRODUCTION

The present invention relates to DNA sequences, comprising nucleic acid fragments encoding dehiscence zone-selective proteins, particularly cell wall hydrolases such as polygalacturonases, the regulatory regions of the corresponding plant genes and their use for modifying dehiscence properties in plants, more particularly pod dehiscence properties in *Brassica napus*.

BACKGROUND OF THE INVENTION

Loss of yield due to seed shedding by mature fruits or pods, also called pod dehiscence or pod shatter, as well as concomitant increase in volunteer growth in the subsequent crop year, are a universal problem with crops that develop dry dehiscent fruits. An economically important crop to which these adverse properties specifically apply is oilseed rape: up to 50% of the potential yield may be lost under adverse weather conditions.

Dry dehiscent fruits, also commonly called pods, may develop from a single carpel (such as the legume in many Fabaceae) or from more than one carpel (such as the silique in many Brassicaceae). In case of the silique, the pod consists of two carpels joined margin to margin. The suture between the margins forms a thick rib, called replum. As pod maturity approaches, the two valves separate progressively from the replum, eventually resulting in the shattering of the seeds that were attached to the replum.

Ultrastructural investigation have demonstrated that pod shatter is associated with the precise degradation of cell wall material at the site of pod valve separation (i.e., the suture). The degradation of the cell wall and loss of cellular cohesion prior to dehiscence is predominantly attributed to solubilization of the middle lamella of the cell wall. This middle lamella is found between primary cell walls and is the cement that holds the individual cells together to form a tissue. Cell separation is preceded by an ethylene climacteric, which temporally correlates with a tissue-specific increase in the activity of the hydrolytic enzyme cellulase (beta-1,4-glucanase) and this occurs specifically in a layer of cells along the suture, which is called the dehiscence zone. In contrast, the activity of the cell wall degrading enzyme polygalacturonase exhibits no correlation either temporally or spatially with pod dehiscence [Meakin and Roberts (1990), *J. Exp. Bot.* 41; 1003]. Pod dehiscence at an early stage of development is characteristic of infestation by the pod midge *Dasineura brassicae*. A localized enhancement of both polygalacturonase and cellulase activity has been observed. However, regulation of midge-induced and maturation-associated shatter was found to be different [Meakin and Roberts (1991), *Annals of Botany* 67: 193].

At first sight, the process of pod dehiscence shares a number of features with abscission wherein plants shed organs, such as leaves, flowers and fruits. It has been observed that ethylene induces or accelerates abscission, whereas auxin inhibits or delays abscission. A decisive step in abscission is the highly coordinated expression, synthesis and secretion of cell wall hydrolytic enzymes in a discrete layer of cells, called the abscission zone. Cellulases (beta-1,4-glucanases) constitute one class of such cell wall hydrolases. Cellulase activity has been identified in various tissues including leaf abscission zones, fruit abscission zones, ripening fruit, senescent cotyledons and styles and anthers [Kemmerer and Tucker (1994), *Plant Physiol.* 104: 557 and references therein]. A second class of hydrolases involved in abscission of mainly fruits are polygalacturonases of which distinctive isoforms have been identified [Bonghi et al. (1992), *Plant Mol. Biol.* 20: 839; Taylor et al. (1990) *Planta* 183: 133].

Kadkol et al. [(1986), *Aust. J. Biol.* 34: 79] reported increased resistance towards shattering in a single, Australian accession of rape. Variation in pod maturation has further been observed in mutants of rape stemming from irradiated seeds [Luczkiewicz (1987), *Proc. 7th Int. Rapeseed Congress* 2: 463]. It can however be concluded that traditional methods for breeding have been unsuccessful in introducing shatter resistance into rape cultivars, without interference in other desirable traits such as early-flowering, maturity and blackleg resistance [Prakash and Chopra (1990), *Genetical Research* 56: 1].

Despite its economic impact very little is known concerning the molecular events and changes in gene expression that occur during oilseed pod dehiscence. At present, two pod-specific mRNAs whose expression is spatially and temporally correlated with pod development have been described. However, the function of the encoded proteins is unknown. [Coupe et al. (1993), *Plant Mol. Biol.* 23: 1223; Coupe et al. (1994), *Plant Mol. Biol.* 24: 223]. PCT publication WO94/23043 in general terms describes an approach for regulating plant abscission and dehiscence.

Accordingly, it is an object of the present invention to provide dehiscence zone-selective genes in plants.

These and other objects are achieved by the present invention, as evidenced by the summary of the invention, description of the preferred embodiments and claims.

SUMMARY OF THE INVENTION

The present invention provides dehiscence zone("DZ")-selective genes of plants, cDNAs prepared from mRNAs encoded by such genes, and promoters of such genes. In particular this invention provides the cDNA of SEQ ID NO:1 and the promoter of a gene encoding a MRNA wherein a cDNA of that mRNA has substantially the nucleotide sequence of SEQ ID NO:1. More particularly, in a preferred embodiment, the present invention relates to the promoter as contained within the 5' regulatory region of SEQ ID NO:14 starting at position 1 and ending at position 2,328.

In another aspect, the present invention also provides DZ-selective chimeric genes, that can be used for the transformation of a plant to obtain a transgenic plant that has modified dehiscence properties, particularly modified pod-dehiscence properties, when compared to plants that do not contain the DZ-selective chimeric gene, due to the expression of the DZ-selective chimeric gene in the transgenic plant.

In yet another aspect, the present invention thus provides a plant containing at least one DZ-selective chimeric gene incorporated in the nuclear genome of its cells, wherein said DZ-selective chimeric gene comprises the following operably linked DNA fragments:

a) a transcribed DNA region encoding:
   1) a RNA which, when produced in the cells of a particular DZ of the plant, prevents, inhibits or reduces the expression in such cells of an endogenous gene of the plant, preferably an endogenous DZ-selective gene, encoding a cell wall hydrolase, particularly an endo-polygalacturonase (an "endoPG"), or, 2) a protein or polypeptide, which when produced in cells of the DZ, kills or disables them or interferes with their normal metabolism, physiology or development, b) a plant expressible promoter which directs expression of the transcribed DNA region at least in cells of the DZ, provided that if the transcribed DNA region encodes a protein or polypeptide, or encodes an antisense RNA or ribozyme directed to a sense RNA encoded by an endogenous plant gene that is expressed in the plant in cells other than those of the DZ, the plant expressible promoter is a DZ-selective promoter, i.e., a promoter which directs expression of the transcribed region selectively in cells of the DZ.

Preferably the transcribed DNA region encodes a protein or polypeptide which is toxic to the cells in which it is produced, such as a barnase; a protein or polypeptide that increases the level of auxins or auxin analogs in the cells in which it is produced, such as a indole-3-acetamide hydrolase and/or a tryptophan monooxygenase; a protein or polypeptide that increases the sensitivity to auxin in the cells in which it is produced, such as the rolB gene product; or a protein or polypeptide that decreases the sensitivity to ethylene in the cells in which it is produced, such as the mutant ETR1-1 protein or another ethylene receptor protein.

In another preferred embodiment of this invention, the transcribed DNA encodes an RNA, such as an antisense RNA or a ribozyme, part of which is complementary to the mRNA encoded by a gene which is naturally expressed in the DZ, preferably a DZ-selective gene.

DETAILED DESCRIPTION OF THE PREFERRED EMBODIMENTS OF THE PRESENT INVENTION

As used herein, the term "dehiscence" refers to the process wherein a plant organ or structure, such as an anther or fruit, opens at maturity along a certain line or in a definite direction, resulting in the shedding of the content of said organ or structure. In some of its aspects the process of dehiscence is reminiscent of the process of abscission, wherein a part or organ, such as a leaf, flower or fruit, is separated from the rest of the plant.

As used herein, the term "pod" means a dry dehiscent fruit that consists of one, two or more carpels. In oilseed rape the pod is a bivalve silique, wherein the valves are delineated by longitudinal dorsal and ventral sutures, which comprise the dehiscence zones.

As used herein, the term "pod dehiscence" means the process wherein a fruit, particularly a pod, splits open along a discrete layer of cells, eventually resulting in the separation of the valves and subsequent shedding of the seeds contained within the fruit, particularly the pod. Pod dehiscence occurs in a large variety of plants that develop dry fruits, such as in most genera of the Cruciferae.

The term "dehiscence zone" (DZ) in its most general sense includes the tissues in the zone along which a plant organ or structure splits open during the process of dehiscence. Macroscopically the DZ can usually be recognized by the presence of a clear suture in the organ. In the strict sense the DZ may comprise a region of only 1–3 parenchymatous cells wide. In a pod, this region usually comprises densely packed cells and is adjacent to the periphery of vascular tissue of the replum separating it from the valve edges. For the purpose of this invention the DZ may also include the cell layers surrounding this region. The DZ extends from the locule of the pod to the epidermal suture.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene regulatory proteins may bind.

As used herein, the term "plant-expressible promoter" means a promoter which is capable of driving transcription in a plant cell. This includes any promoter of plant origin, but also any promoter of non-plant origin which is capable of directing transcription in a plant cell, i.e., certain promoters of viral or bacterial origin such as the CaMV 35S or the T-DNA promoters.

The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or promoter region) is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

As used herein, the term "cell wall hydrolase" means an enzyme that is involved in the degradation of cell wall material, e.g., during the process of dehiscence. Examples of such enzymes include, but are not limited to, polygalacturonase, cellulase (beta-1,4-glucanase), beta-galactosidase, proteases hydrolyzing cell wall proteins, and the like.

The term "gene" means any DNA fragment comprising a DNA region (the "transcribed DNA region") that is transcribed into a RNA molecule (e.g., a mRNA) in a cell under control of suitable regulatory regions, e.g., a plant expressible promoter. A gene may thus comprise several operably linked DNA fragments such as a promoter, a 5' untranslated leader sequence, a coding region, and a 3' untranslated region comprising a polyadenylation site. An endogenous plant gene is a gene which is naturally found in a plant species. A chimeric gene is any gene which is not normally found in a plant species or, alternatively, any gene in which the promoter is not associated in nature with part or all of the transcribed DNA region or with at least one other regulatory regions of the gene.

The term "expression of a gene" refers to the process wherein a DNA region under control of regulatory regions, particularly the promoter, is transcribed into an RNA which is biologically active i.e., which is either capable of interaction with another nucleic acid or which is capable of being translated into a biologically active polypeptide or protein. A gene is said to encode an RNA when the end product of the expression of the gene is biologically active RNA, such as an antisense RNA or a ribozyme. A gene is said to encode a protein when the end product of the expression of the gene is a biologically active protein or polypeptide.

The phenotypic effect of expression of a gene refers to the biochemical, physiological and/or developmental effects of the production of the RNA or protein, encoded by the gene, on the plant cells (or plants) in which it is produced.

Phenotypic effects of gene expression may be reduced or prevented by reducing or preventing the production of the encoded RNA or protein, or by otherwise interfering with the biological activity of such RNA or protein.

As defined herein, whenever it is stated in the specification that a "cDNA of such mRNA comprises the nucleotide sequence of SEQ ID NO:X" the RNA thus has the same nucleotide sequence as represented in SEQ ID NO:X except that the U-residues (in the RNA sequence) are replaced by T-residues (in the DNA sequence).

In accordance with this invention, DZ-selective cDNAs and their corresponding plant genomic DNA fragments are identified as follows:

1) a cDNA library is constructed starting from mRNA isolated from DZ tissue and the CDNA library is subjected to differential screening in order to identify an mRNA which is selectively present in tissues of a particular DZ when compared to other plant tissues including but not limited to: pod walls, seeds, replum, leaves, stems, roots, reproductive organs, and the like. Alternatively, the cDNA library is screened with oligonucleotides, that are deduced from a determined amino acid sequence of an isolated protein, such as, for example, a cell wall hydrolase, that is identified to be selectively present in the DZ. Furthermore, it is possible to use the same oligonucleotides in a nested-PCR approach and to use the amplified fragment(s) as a probe to screen the library. The DZ-selective cDNA library can be constructed from a pool of mRNAs, isolated at different stages of DZ development;

2) a cDNA, encoding the DZ-selective mRNA or protein, is isolated and characterized;

3) this cDNA is used as a probe to identify and isolate the region in the plant genome, comprising the nucleotide sequence encoding the DZ-selective mRNA or protein. Alternatively, the genomic DNA can be isolated utilizing inverse PCR using oligonucleotides deduced from the cDNA sequence; and 4) optionally, RNA probes corresponding to the cDNAs are constructed and used in conventional RNA-RNA in-situ hybridization analysis [see e.g., De Block et al. (1993), *Anal. Biochem.* 215: 86] of different plant tissues, including the particular DZ of interest, to confirm the selective presence of the mRNA produced by the presumed DZ-selective endogenous plant gene in that DZ.

The term "dehiscence zone-selective", with respect to the expression of a DNA in accordance with this invention, refers to, for practical purposes, the highly specific, preferably exclusive, expression of a DNA in cells of one particular DZ, particularly a pod DZ, or a limited series of DZs.

Thus a DZ-selective gene is an endogenous gene of a plant that is selectively expressed in the cells of certain dehiscence zones, particularly in the cells of the pod dehiscence zone of the plant. Any plant which possesses the DZ of interest may be used for the isolation of DZ-selective genes. Suitable plants for the isolation of DZ-selective genes are plants of the family Cruciferae including but not limited to *Arabidopsis thaliana, Brassica campestds, Brassica juncea,* and especially *Brassica napus;* plants of the family Leguminosae including but not limited to *Glycine max, Phaseolus vulgans* and the like. The mRNA (or the cDNA obtained thereof) transcribed from such a gene is a DZ-selective mRNA (or cDNA). A promoter that drives and controls the transcription of such a mRNA is referred to as a DZ-selective promoter. A DZ-selective promoter can for instance be used to express a cytotoxic gene (e.g., a barnase gene) in a plant so that normal growth and development, and agronomical performance (as measured for instance by seed yield) of the plant is not negatively affected by expression of the cytotoxic gene in cells other than the DZ cells, preferably in cells other than the pod DZ cells.

Once the DZ-selective gene (i.e., the genomic DNA fragment, encoding the DZ-selective mRNA from which the DZ-selective cDNA can be prepared) is obtained, the promoter region containing the DZ-selective promoter is determined as the region upstream (i.e., located 5' of) from the codon coding for the first amino acid of the protein encoded by the mRNA. It is preferred that such promoter region is at least about 400 to 500 bp, preferably at least about 1000 bp, particularly at least about 1500 to 2000 bp, upstream of the start codon. For convenience, it is preferred that such promoter region does not extend more than about 3000 to 5000 bp upstream of the start codon. The actual DZ-selective promoter is the region of the genomic DNA. upstream (i.e., 5') of the region encoding the DZ-selective mRNA. A chimeric gene comprising a DZ-selective promoter operably linked to the coding region of the gus gene [Jefferson et al. (1986), *Proc. Natl. Acad. Sci. USA* 83: 8447] will selectively produce, in transgenic plants, detectable beta-glucuronidase activity (encoded by the gus gene)in the cells of the particular DZ of interest, as assayed by conventional in-situ histochemical techniques [De Block and Debrouwer (1992), *The Plant Journal* 2:261; De Block and Debrouwer (1993), *Planta* 189: 218].

Preferred DZ-selective genes from which DZ-selective promoters can be obtained, are genes, preferably Brassica napus genes, that encode a DZ-selective mRNA from which a cDNA can be prepared that contains the sequence corresponding to the sequence of oligonucleotide PG1 (SEQ ID NO:3) between nucleotide positions 11 and 27 and/or the sequence of oligonucleotide PG3 (SEQ ID NO:5) between nucleotide positions 11 and 27(i.e., starting at position 11 and ending at position 27); and/or contains the sequence complimentary to the oligonucleotide PG2 (SEQ ID NO:4) between nucleotide positions 11 and 25 and/or the sequence of the oligonucleotide PG5 (SEQ ID NO:6) between nucleotide positions 11 and 27. Preferably, such DZ-selective cDNA contains aforementioned sequences of oligonucleotides PG1 and PG3 and PG2 and PG5, or encodes a protein encoded by the region of SEQ ID NO:1 between nucleotide positions 95 and 1,393.

A particularly preferred DZ-selective gene is the *Brassica napus* gene that encodes a DZ-selective mRNA from which a cDNA can be prepared that contains the sequence of SEQ ID NO:1 at least between nucleotides 10 and 1600. Another preferred DZ-selective gene is the *Brassica napus* gene, that encode a DZ-selective mRNA from which a cDNA can be prepared that contains the sequence of SEQ ID NO:11.

A preferred promoter of the present invention is the promoter contained in the 5' regulatory region of a genomic clone corresponding to the cDNA of SEQ ID NO:1, e.g., the 5' regulatory region with the sequence of SEQ ID NO:14 starting at position 1 and ending at position 2,328. A more preferred promoter region is the DNA fragment comprising the sequence of SEQ ID NO:14 starting anywhere between the unique SphI site (positions 246–251) and the HindII site (positions 1,836–1,841), particularly between the SphI site and the BamHI site (positions 1,051–1,056), and ending at nucleotide position 2,328 (just before the ATG translation start codon). Such a promoter region comprises the DZ-selective promoter of the subject invention and the 5' untranslated leader region and is used for the construction of DZ-selective chimeric genes. In this regard a more preferred promoter region is the DNA fragment (hereinafter referred to as "PDZ") with the sequence of SEQ ID NO:14 between positions 251 (the SphI site) and 2,328.

However, smaller DNA fragments can be used as promoter regions in this invention and it is assumed that any fragment of the DNA of SEQ ID NO:14 which comprises at least the about 490 basepairs, more preferably at least about 661 basepairs and most preferably about 1326 basepairs, upstream from the translation inititation codon can be used. Particularly preferred smaller fragments to be used as promoter region in this invention have a DNA sequence comprising the sequence of SEQ ID NO:14 between the nucleotides 1002 and 2328.

It is assumed that the DZ-specificity of the promoter of the 5' regulatory region of SEQ ID NO:14 can be considerably improved by inclusion of the nucleotide sequence of SEQ ID NO:14 between nucleotides 1002 and 1674. Therefore promoters comprising this nucleotide sequence are particularly preferred.

Alternatively, artificial promoters can be constructed which contain those internal portions of the promoter of the 5' regulatory region of SEQ ID NO:14 that determine the DZ-selectivity of this promoter. These artifical promoters can contain a "core promoter" or "TATA box region" of another promoter capable of expression in plants, such as a CaMV 35S "TATA box region" as described in WO 93/19188. Suitable promoter fragments or artificial promoters can be identified, for example, by their approriate fusion to a reporter gene (such as the gus gene) and the detection of the expression of the reporter gene in the appropriate tissue(s) and at the appropriate developmental stage. It is known that such smaller promoters and/or artificial promoters comprising those internal portions of the 5' regulatory region of SEQ ID NO:14 that determine the DZ selectivity can provide better selectivity of transcription in DZ-specific cells and/or enhanced levels of transcription of the transcribed regions of the DZ-selective chimeric genes of the invention.

Besides the actual promoter, the 5' regulatory region of the DZ-selective gene of this invention also comprises a DNA fragment encoding a 5' untranslated leader (5'UTL) sequence of an RNA located between the transcription start site and the translation start site. It is assumed that the 5' transcription start site is located between position 2,219 and 2,227 (in SEQ ID NO:14), resulting in a 5'UTL of about 102 to 110 nucleotides in length. It is also assumed that this region can be replaced by another 5'UTL, such as the 5'UTL of another plant-expressible gene, without substantially affecting the specificity of the promoter.

Other useful DZ-selective genes or cDNAs for use in this invention are those isolated from other sources, e.g., from other cultivars of *B. napus* or even from other plant species, for instance by using the cDNA of SEQ ID NO:1 (or SEQ ID NO:11) as a probe to screen genomic libraries under high stringency hybridization conditions using conventional methods as described in *Nucleic Acid Hybridization: A Practical Approach* (1985), IRL Press Ltd UK (Eds. B. D. Hames and S. J. Higgins). A useful gene for the purpose of this invention is thus any gene characterized by encoding a mRNA from which a cDNA variant can be prepared that contains a coding region with a nucleotide sequence that is essentially similar to that of the coding region of the cDNA clone of SEQ ID NO:1, and coding for a protein with polygalacturonase activity. Also promoter regions and promoters can be identified, for example, using such cDNA variants, which are essentially similar to a promoter region or promoter with a sequence as contained in SEQ ID NO:14.

With regard to nucleotide sequences (DNA or RNA), such as sequences of cDNAs or of regulatory regions of a gene, "essentially similar" means that when two sequences are aligned, the percent sequence identity—i.e., the number of positions with identical nucleotides divided by the number of nucleotides in the shorter of the two sequences—is higher than 80%, preferably higher than 90%, especially with regard to regulatory regions. The alignment of the two nucleotide sequences is performed by the Wilbur and Lipmann algorithm [Wilbur and Lipmann (1983), *Proc. Nat. Acad. Sci. U.S.A.* 80: 726] using a window-size of 20 nucleotides, a word length of 4 nucleotides, and a gap penalty of 4.

Two essentially similar cDNA variants will typically encode proteins that are essentially similar to each other. For example, a variant of the cDNA of SEQ ID NO:1 will typically encode a protein with an amino acid sequence which is essentially similar to the amino acid sequence of the protein encoded by the cDNA of SEQ ID NO:1. With regard to "amino acid sequences", essentially similar means that when the two relevant sequences are aligned, the percent sequence identity—i.e., the number of positions with identical amino acid residues divided by the number of residues in the shorter of the two sequences—is higher than 80%, preferably higher than 90%. The alignment of the two amino acid sequences is performed by the Wilbur and Lipmann algorithm [Wilbur and Lipmann (1983), *Proc. Nat. Acad. Sci. U.S.A.* 80: 726] using a window-size of 20 amino acids, a word length of 2 amino acids, and a gap penalty of 4. Computer-assisted analysis and interpretation of sequence data, including sequence alignment as described above, can be conveniently performed using the programs of the Intelligenetics™ Suite (Intelligenetics Inc., CA).

In accordance with this invention, the DZ-selective cDNAs and genomic DNAs, as well as the regulatory regions obtained from the genomic DNAs are used to modify the dehiscence properties in plants, particularly pod dehiscence properties in *Brassica napus*.

Thus, in accordance with this invention, a recombinant DNA is provided which comprises at least one DZ-selective chimeric gene comprising a plant expressible promoter and a transcribed DNA region, one or both of which is derived from a DZ-selective gene of this invention.

Expression of a DZ-selective chimeric gene in a transgenic plant will have phenotypic effects only in the cells of the DZ. Thus, expression of a DZ-selective gene may selectively prevent, suppress, inhibit or reduce the phenotypic effects of expression of endogenous plant genes in a certain dehiscence zone (such as a pod DZ), may selectively kill or disable cells of the dehiscence zone, or may interfere with the normal metabolism of DZ cells, resulting in the delay or prevention of dehiscence, particularly pod dehiscence. For the purpose of this invention, a plant cell (such as a DZ cell) is killed or disabled if either all biochemical and/or physiological processes of the cell are stopped or, alternatively, if the biochemical and/or physiological processes of the cell are changed to effectively reduce the extracellular production of at least one enzyme involved in the degradation of plant cell walls, particularly a pectin degrading enzyme such as a polygalacturonase, preferably by at least 30%, particularly by at least 75%, more particularly by at least 90%.

For the purpose of the present invention, the phenotypic effects of expression of an endogenous gene in a plant cell is prevented, suppressed, inhibited or reduced if the amount of mRNA and/or protein produced by the cell by expression of the endogenous gene is reduced, preferably by at least 30%, particularly by at least 75%, more particularly by at least 90%.

Plants, in which dehiscence is delayed to different extents, or even prevented, are produced by transforming a plant with a recombinant DNA comprising at least one DZ-selective chimeric gene of this invention whose expression in the plant results in the production of RNA or a protein or polypeptide which interferes to different degrees with the normal functioning of the cells of the dehiscence zone, for example, by reducing the phenotypic effects of expression of one or more endogenous genes that encode cell wall hydrolytic enzymes, or by killing the DZ cells. A delay in the onset of dehiscence, particularly fruit dehiscence, whereby pre-harvest shattering of seeds can be reduced or prevented, will find its application in those plants that suffer from premature (i.e., prior to harvest) seed loss.

In a preferred embodiment of the present invention the DZ-selective chimeric gene comprises a transcribed DNA region which is transcribed into an RNA the production of which in the cells of the DZ reduces, inhibits or prevents the expression of an endogenous gene, preferably a gene encoding a cell wall hydrolase, particularly an endo-polygalacturonase, in the cells of the DZ. The reduction of the expression of the endogenous gene can be demonstrated by the reduction of the cytoplasmic levels of the mRNA normally produced by the endogenous gene. The endogenous gene as isolated from the plant will hereinafter be designated as the sense gene which encodes a sense mRNA (or sense pre-mRNA, i.e., an unprocessed mRNA which may include intron regions).

It is preferred that the endogenous sense gene encodes an enzyme involved in cell wall hydrolysis, preferably a pectin-degrading enzyme, such as a pectin esterase, a pectin methyl esterase, a pectin lyase, a pectate lyase, a polygalacturonase and the like, and particularly an endo-PG. It is believed that pectin degrading enzymes, particularly endo-polygalacturonases, play an important role in the degradation of the middle lamella material of plant cell walls and in the process of dehiscence, and that selective inhibition of the production of such enzymes in the dehiscence zone or in the region surrounding the dehiscence zone (e.g., by expression of an antisense RNA to the endo-PG encoding mRNA) on the average delays pod shatter for at least 1 day, preferably 2–5 days.

Although the sense gene may encode any cell wall hydrolase, that is secreted by the cells of the DZ during the process of dehiscence, and that is involved in the degradation of cell wall material in a certain dehiscence zone, such as for example a cellulase, a glucanase, or a beta-galactosidase, it is preferred that the sense gene is an endogenous DZ-selective gene.

Thus, in one aspect of this invention the DZ-selective chimeric gene of this invention encodes an antisense RNA which is complementary to at least part of a sense mRNA or sense pre-mRNA. Such antisense RNA is said to be directed to the sense RNA (or sense pre-mRNA). In this regard, the encoded antsense RNA comprises a region which is complementary to a part of the sense mRNA or sense pre-mRNA, preferably to a continuous stretch thereof of at least 50 bases in length, preferably of at least between 100 and 1000 bases in length. The upper limit for the length of the region of the antisense RNA which is complementary to the sense RNA is of course the length of the full-length sense pre-mRNA, or to the full length sense mRNA (which may or may not be processed from a sense pre-mRNA), produced by the plant cells can be used. However, the antisense RNA can be complementary to any part of the sequence of the sense pre-mRNA and/or of the processed sense mRNA: it may be complementary to the sequence proximal to the 5' end or capping site, to part or all of the 5' untranslated region, to an intron or exon region (or to a region bridging an exon and intron) of the sense pre-mRNA, to the region bridging the noncoding and coding region, to all or part of the coding region including the 3' end of the coding region, and/or to all or part of the 3' untranslated region. In case the sense gene is a member of a gene family, it is preferred that the antisense RNA encoded by the DZ-selective chimeric gene of this invention contains a sequence which is complementary to a region of the sense RNA, e.g., a DZ-selective sense RNA, of at least 50 nucleotides and which has a percent sequence identity (see above) of less than 50%, preferably less than 30%, with any region of 50 nucleotides of any sense RNA encoded by any other member of the gene family.

The transcribed DNA region in the DZ-selective chimeric gene of this invention can also encode a specific RNA enzyme, or so-called ribozyme (see, e.g., WO89/05852), capable of highly specific cleavage of the sense mRNA or sense pre-RNA. Such ribozyme is said to be directed to the sense RNA (or sense pre-mRNA).

Expression of the endogenous gene producing a sense mRNA in a plant can also be inhibited or repressed by a DZ-selective chimeric gene which encodes part or all, preferably all, of such sense RNA [Jorgensen et al. (1992), *AgBiotech News Info* 4: 265N].

The sense RNA to which the antisense RNA or ribozyme encoded by the DZ-selective chimeric gene of this invention is directed is preferably a mRNA, wherein a (doublestranded) cDNA of such mRNA comprises the nucleotide sequence of SEQ ID NO:1 (or SEQ ID NO:11) or variants thereof. A preferred region of the cDNA corresponding to the sense RNA to which the antisense RNA or ribozyme encoded by the DZ-selective chimeric gene of this invention is directed comprises a nucleotide sequence of SEQ ID NO:1 starting anywhere between nucleotide 890 and 950 and ending anywhere between nucleotide 1560 and 1620, such as, but not limited to, the nucleotide sequence between nucleotides 952 and 1607. Another preferred region of the cDNA corresponding to the sense RNA to which the antisense RNA or ribozyme encoded by the DZ-selective chimeric gene of this invention is directed comprises a nucleotide sequence of SEQ ID NO:1 starting anywhere between nucleotide 1280 and 1340 and ending anywhere between nucleotide 1560 and 1620, such as, but not limited to, the nucleotide sequence between nucleotides 1296 and 1607.

A DZ-selective chimeric gene encoding a antisense RNA or ribozyme, as described above, is preferably under the control of a DZ-selective promoter. Particularly useful DZ-selective promoters are the promoters from the DZ-selective genes described above, particularly the promoter as conained within the 5' regulatory region of SEQ ID NO:14 between position 1 and 2,328. However, if the DZ-selective gene encodes an antisense RNA and/or ribozyme which is directed to a sense RNA produced by an endogenous DZ-selective gene, preferably a gene encoding a endo-polygalacturonase, it is not required that the promoter of the DZ-selective chimeric gene be a DZ-selective promoter. Nevertheless, in such case the promoter of the DZ-selective gene should direct expression at least in cells of the DZ. Indeed, because the sense RNA is produced selectively in the cells of the DZ, the production of the antisense RNA or ribozyme encoded by the DZ-selective gene in cells other than the cells of the DZ, will not have a noticeable phenotypic effect on such cells. Examples of promoters that direct expression at least in cells of the DZ are constitutive plant expressible promoters such as the promoter (P35S) of the 35S transcript of Cauliflower mosaic virus (CaMV)[Guilley et al. (1982), *Cell* 30: 763], or the promoter (Pnos) of the nopaline synthase gene of *Agrobacterium tumefaciens* [Depicker et al. (1982), *J. Mol. Appl. Genet.* 1: 561].

In another preferred embodiment of this invention, the DZ-selective chimeric gene encodes a mRNA which, when produced in plant cells, is translated into a protein or polypeptide which interferes with the metabolism and/or physiology of the plant cells. In most cases production of such protein or polypeptide will be undesired in cells other than the DZ cells and in this regard it is preferred that such chimeric genes comprise a DZ-selective promoter. Particular useful DZ-selective promoters are again the promoters from the DZ-selective genes described above.

In one aspect of this invention the DZ-selective chimeric gene of this invention comprises a transcribed DNA region encoding a protein the activity of which will result in an increase in biologically active auxins or auxin analogs within the cells. Such protein may for instance be involved in auxin biosynthesis, such as tryptophan monooxygenase and/or the indole-3-acetamide hydrolase, encoded by the *Agrobacterium tumefaciens* T-DNA gene 1 (iaaM) and/or gene 2 (iaaH), respectively [Gielen et al. (1984), *The EMBO J.* 3: 835], or may be the amidohydrolase, encoded by the *Arabidopsis thaliana* ILR1 gene, which releases active indole-3-acetic acid (IAA) from IAA-conjugates [Bartel and Fink (1995), *Science* 268: 1745]. In view of the observed decline in IAA levels prior to pod dehiscence (see Example 1), it is thought that production of such auxin increasing proteins selectively in the DZ cells of a plant, will not result in the killing of the cells due to overproduction of IAA, but will rather result in the maintenance and/or restoration of the IAA levels substantially as found before the observed decline. This delays the onset of pod dehiscence, through a prolonged inhibition by IAA of production and/or activity of cell wall hydrolytic enzyme normally produced by the cells in the dehiscence zone.

Alternatively the transcribed DNA region of the DZ-selective chimeric gene of this invention can comprise the open reading frame of the *Agrobacterium rhizogenes* rolB gene [Furner et al. (1986), *Nature* 319: 422]. Expression of such DZ-selective chimeric gene in a plant will result in an increase of the sensitivity of the plant cells towards auxin through the production of the rolB gene product in cells of the pod DZ thereby countering the normal decline in IAA concentration in the DZ prior to pod shattering.

In another aspect of the present invention, the DZ-selective chimeric gene of this invention comprises a transcribed DNA region encoding a protein, the activity of which results in a decrease of the sensitivity towards ethylene of the plant cells in which it is produced. Indeed, several genes involved in the ethylene signal transduction pathway in plants have been identified by mutational analysis (e.g., ETR1, ETR2, EIN4, ERS, CTR1, EIN2, EIN3, EIN5, EIN6, HLS1, EIR1, AUX1, EIN7)and for a number of them, the corresponding genes have been cloned [Chang (1996), *TIBS* 21:129; Bleecker and Schaller (1996), *Plant Physiol* 111:653]. It is thought that ETR1, ETR2, EIN4, ERS all encode ethylene receptors, while the rest of the genes would be involved in the ethylene signal transduction pathway downstream of the receptors [Ecker (1995), *Science* 268: 667]. The ethylene receptors which have been sequenced, bear homology to the receiver domain of the response regulator component and/or to the histidine protein kinase domain of the sensor component of the so-called bacterial two-component regulators and are divided in two classes according to the presence or absence of the receiver domain homology. Class I ethylene receptors comprise both the sensor and receiver homologous domains and are exemplified by ETR1 (Arabidopsis), and eTAE1 (tomato). Class II ethylene receptors comprise only the domain homologous to the histidine protein kinase domain of the sensor component and are exemplified by ERS (Arabidopsis) and NR (tomato). Receptors encoded by mutant alleles of the identified genes confer a dominant insensitivity to ethylene [Chang (1996), supra; Bleecker and Schaller (1996), supra]. Therefore, an example of a DZ-selective chimeric gene, comprising a transcribed DNA region encoding a protein whose activity results in a decrease of the sensitivity towards ethylene of the plant cells in which it is produced, is one which comprises the open reading frame of a dominant, ethylene-insensitive, mutant allele of the *Arabidopsis thaliana* ETR1 gene, such as ETR1-1 [Chang et al. (1993),*Science* 262: 539]. A plant in which such DZ-selective chimeric gene is expressed produces a mutant ethylene receptor (the ETR1-1 protein) selectively in the cells of the DZ and these cells therefore become insensitive towards the phytohormone ethylene and do not respond (metabolically) to changes in the concentration of the hormone, such as the ethylene climacteric observed prior to the onset of pod dehiscence. It is thought that alternatively, a transcribed DNA region comprising an open reading frame of a dominant, ethylene-insensitive, mutant allele of any one of the mentioned class I ethylene receptors can be used to the same effect. In another example of such a DZ-selective chimeric gene, conferring ethylene-insensitivity to the plants cells expressing the DZ-selective chimeric gene, a transcribed DNA region comprising an open reading frame of a dominant, ethylene-insensitive, mutant allele of any one of the mentioned class II ethylene receptors, such as the *Arabidopsis thaliana* ERS gene [Hua et al. (1995), *Science* 269: 1712] or the omato NR gene [Wilkinson et al. (1995), *Science* 270:1807] can be used for the same purpose.

It is further assumed that the rest of the products encoded by the genes, involved in the ethylene signal transduction pathway, mentioned above, act downstream of the receptors. For CTR1, EIN2 and EIN3 the genes have been cloned [Ecker (1995), *Science* 268: 667]. Modulation of the expression of the latter genes in the dehiscence zone, e.g., by antisense RNA or ribozyme RNA, transcribed under control of a DZ-specific promoter, which is targetted towards the mentioned genes, will also influence the sensitivity towards ethylene.

In another aspect of this invention the DZ-selective chimeric gene of this invention comprises a transcribed DNA region encoding a protein or polypeptide which, when produced in a plant cell, such as a cell of a pod DZ, kills such cell or at least interferes substantially with its metabolism, functioning or development. Examples of such transcribed DNA regions are those comprising DNA sequences encoding ribonucleases such as RNase T1 and especially barnase [Hartley (1988), *J. Mol. Biol.* 202: 913]; cytotoxins such as the A-domain of diphtheria toxin [Greenland et al. (1983), *Proc. Natl. Acad. Sci. USA* 80: 6853] or the *Pseudomonas exotoxin* A. Several other DNA sequences encoding proteins with cytotoxic properties can be used in accordance with their known biological properties. Examples include, but are not limited to, DNA sequences encoding proteases such as papain; glucanases; lipases such as phospholipase A2; lipid peroxidases; methylases such as the *E. coli* Dam methylase; DNases such as the EcoRI endonuclease; plant cell wall inhibitors, and the like.

In still another aspect of this invention the DZ-selective chimeric gene of this invention comprises a transcribed DNA region encoding a protein or polypeptide which is capable of being secreted from plant cells and of inhibiting at least the activity of at least one endo-polygalacturonase that is produced in a dehiscence zone (such as a pod DZ), particularly the endo-PG encoded by the cDNA of SEQ ID NO:1.

In the DZ-selective chimeric gene of this invention it is preferred that the 5' untranslated region of encoded RNA is normally associated with the promoter, such as a DZ-selective promoter, of the chimeric gene. However, the 5' untranslated region may also be from another plant expressible gene. Thus, it is preferred that a DZ-selective chimeric gene of this invention comprises the complete 5' regulatory region (including the 5' untranslated region) of a DZ-selective gene. A particularly useful 5' regulatory region is a region of SEQ ID NO:14, immediately upstream of position 1,329, preferably a region of at least 490 bp, more preferably a region extending to the first SphI site upstream of position 2,329.

The DZ-selective chimeric genes of this invention preferably also comprise 3' untranslated regions, which direct correct polyadenylation of mRNA and transcription termination in plant cells. These signals can be obtained from plant genes such as polygalacturonase genes, or they can be obtained from genes that are foreign to the plants. Examples of foreign 3' transcription termination and polyadenylation signals are those of the octopine synthase gene [De Greve et al. (1982), *J. Mol. Appl. Genet.* 1: 499], of the nopaline synthase gene [Depicker et al. (1982), *J. Mol. Appl. Genet.* 1: 561] or of the T-DNA gene 7 [Velten and Schell (1985), *Nucl. Acids Res.*13: 6998] and the like.

Preferably, the recombinant DNA comprising the DZ-selective chimeric gene also comprises a conventional chimeric marker gene. The chimeric marker gene can comprise a marker DNA that is; under the control of, and operatively linked at its 5' end to, a plant-expressible promoter, preferably a constitutive promoter, such as the CaMV 35S promoter, or a light inducible promoter such as the promoter of the gene encoding the small subunit of Rubisco; and operatively linked at its 3' end to suitable plant transcription termination and polyadenylabon signals. The marker DNA preferably encodes an RNA, protein or polypeptide which, when expressed in the cells of a plant, allows such cells to be readily separated from those cells in which the marker DNA is not expressed. The choice of the marker DNA is not critical, and any suitable marker DNA can be selected in a well known manner. For example, a marker DNA can encode a protein that provides a distinguishable color to the transformed plant cell, such as the A1 gene (Meyer et al. (1987), *Nature* 330: 677), can provide herbicide resistance to the transformed plant cell, such as the bar gene, encoding resistance to phosphinothricin (EP 0,242, 246), or can provided antibiotic resistance to the transformed cells, such as the aac(6') gene, encoding resistance to gentamycin (WO94/01560).

The DZ-selective promoters of this invention are believed to be highly specific in activity or effect with regard to directing gene expression in cells of the DZ. However the characteristics (e.g., tissue-specificity) of a promoter contained in a chimeric gene may be slightly modified in some plants that are transformed with such chimeric gene. This can, for example, be attributed to "position effects" as a result of random integration in the plant genome.

Therefore in some plants transformed with the DZ-selective chimeric gene of this invention low-level expression of the chimeric gene may be observed in certain non-DZ cells. Thus, optionally, the plant genome can also be transformed with a second chimeric gene comprising a second transcribed DNA region, that is under control of a second plant-expressible promoter and that encodes a RNA, protein or polypeptide which is capable of counteracting, preventing or inhibiting the activity of the gene product of the DZ-selective chimeric gene. If the DZ-selective chimeric gene encodes barnase it is preferred that the second chimeric gene encodes a barstar, i.e., an inhibitor of barnase [Hartley (1988), *J. Mol. Biol.* 202: 913]. Other useful proteins encoded by the second chimeric genes are antibodies or antibody fragments, preferably single chain antibodies, that are capable of specific binding to the protein encoded by the DZ-selective chimeric gene whereby such protein is biologically inactivated.

Preferably the second promoter is capable of driving expression of the second transcribed DNA region at least in non-DZ cells of the plant to counteract, prevent or inhibit the undesired effects of low expression of the DZ-selective chimeric gene in such cells in some transformed plants. Examples of useful second promoters are the CaMV minimal 35S promoter [Benfey and Chua (1990), *Science* 250: 959] or the promoter of the nopaline synthase gene of *Agrobacterium tumefaciens* T-DNA [Depicker et al. (1982), *J. Mol. Appl. Genet.* 1: 561]. Other useful promoters are promoters from genes that are known not to be active in the DZ, such as Brassica napus genes encoding a mRNA from which a CDNA can be prepared that comprises the sequence of SEQ ID. NO:8, SEQ ID NO:10 or SEQ ID. NO:12.

In plants the second chimeric gene is preferably in the same genetic locus as the DZ-selective chimeric gene so as to ensure their joint segregation. This can be obtained by combining both chimeric genes on a single transforming DNA, such as a vector or as part of the same T-DNA. However, in some cases a joint segregation is not always desirable. Therefore both constructs can be present on separate transforming DNAs, so that transformation might result in the integration of the two constructs at different location in the plant genome.

In still a further embodiment of the present invention, a plant with modified dehiscence properties can be obtained from a single plant cell by transforming the cell in a known manner, resulting in the stable incorporation of a DZ-selective chimeric gene of the invention into the nuclear genome.

A recombinant DNA comprising a DZ-selective chimeric gene can be stably incorporated in the nuclear genome of a cell of a plant, particularly a plant that is susceptible to Agrobacterium-mediated transformation. Gene transfer can be carried out with a vector that is a disarmed Ti-plasmid, comprising a DZ-selective chimeric gene of the invention, and carried by Agrobacterium. This transformation can be carried out using the procedures described, for example, in EP 0,116,718. Ti-plasmid vector systems comprise a DZ-selective chimeric gene between the T-DNA border sequences, or at least to the left of the right T-DNA border. Alternatively, any other type of vector can be used to transform the plant cell, applying methods such as direct gene transfer (as described, for example, in EP 0,233,247), pollen-mediated transformation (as described, for example, in EP 0,270,356, WO085/01856 and U.S. Pat. No. 4,684, 611), plant RNA virus-mediated transformation (as described, for example, in EP 0,067,553 and U.S. Pat. No. 4,407,956), liposome-mediated transformation (as described, for example, in U.S. Pat. No. 4,536,475), and the like.

Other methods, such as microprojectile bombardment as described, for example, by Fromm et al. [(1990), Bio/Technology 8: 833] and Gordon-Kamm et al. [(1990), The Plant Cell 2: 603], are suitable as well. Cells of monocotyledonous plants, such as the major cereals, can also be transformed using wounded or enzyme-degraded intact tissue capable of forming compact embryogenic callus, or the embryogenic callus obtained thereof, as described in WO92/09696. The resulting transformed plant cell can then be used to regenerate a transformed plant in a conventional manner.

The obtained transformed plant can be used in a conventional breeding scheme to produce more transformed plants with the same characteristics or to introduce the DZ-selective chimeric gene of the invention in other varieties of the same or related plant species. Seeds obtained from the transformed plants contain the DZ-selective chimeric gene of the invention as a stable genomic insert.

The following Examples describe the isolation and characterization of a DZ-selective gene from Brassica napus, the identification of DZ-selective promoter, and the use of such a promoter for the modification of dehiscence properties in plants. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

In the examples and in the description of the invention, reference is made to following sequences of the Sequence Listing:

| SEQ ID NO: 1 | DZ-selective cDNA encoding a enco-polygalacturonase of Brassica napus |
|---|---|
| SEQ ID NO: 3 | oligonucleotide PG1 |
| SEQ ID NO: 4 | oligonucleotide PG2 |
| SEQ ID NO: 5 | oligonucleotide PG3 |
| SEQ ID NO: 6 | oligonucleotide PG5 |
| SEQ ID NO: 7 | PCR Fragment BPG32-26 |
| SEQ ID NO: 8 | PCR Fragment KPG32-8 |
| SEQ ID NO: 9 | PCR Fragment LPG12-16 |
| SEQ ID NO: 10 | PCR Fragment LPG32-24 |
| SEQ ID NO: 11 | PCR Fragment LPG32-25 |
| SEQ ID NO: 12 | PCR Fragment LPG32-32 |
| SEQ ID NO: 13 | T-DNA of pGSV5 |
| SEQ ID NO: 14 | sequence of genomic clone comprising the DZ-selective promoter region driving expression of an endopolygalacturonase gene of Brassica napus |

In order to further illustrate the present invention and advantages thereof, the following specific examples are given, it being understood that the same are intended as illustrative and in nowise limitative.

EXAMPLE 1

Characterization of Pod Dehiscence During Pod Development

Endogenous Phytohormone Profiles During Pod Development

Brassica napus cv Fido plants were grown in an unheated greenhouse. At 12 days after germination plants were transferred to, and further grown in, 1000 cm3 compost. Pods were collected at one week intervals from two to eight weeks after anthesis. The pods were taken from the base of the terminal one of the first three axillary racemes. The pods were separated into dehiscence zone, pod wall and seeds.

The samples were ground with a mortar and pestle and then extracted for 16 hours at −20° C. in a total volume of 80% methanol. Purification and analysis of phytohormones was carried out essentially as described [Bialek and Cohen (1989), Plant Physiol. 90: 398; Prinsen et al. (1991), in: A Laboratory Guide for Cellular and Molecular Plant Biology. Ed. Negrutiu and Gharti-Chhetri. Birkhäuser Verlag, Basel/Boston/Berlin pp. 175–185, pp.323–324; Chauvaux et al. (1993), J. Chromatogr. A 657: 337].

Different parts of the pods (pod wall, dehiscence zone and seeds) were screened for endogenous concentrations of the ethylene precursor 1-aminocyclopropane-1-carboxylic acid (ACC) and conjugates thereof as well as for indole-3-acetic acid (IAA) and conjugates thereof.

A peak in ethylene evolution [see also Meakin and Roberts (1990), J. Exp. Bot. 41: 1003] was observed immediately before pod shattering; this peak was correlated with observed peaks of free ACC. Especially in the dehiscence zone a decline in IAA concentrations (free as well as conjugated forms) was observed, just before the onset of pod opening. This decline in IAA concentration was specifically correlated with an increased cellulase activity in the dehiscence zone.

In a further experiment ethylene production was inhibited by treating the pods with aminoethoxyvinylglycine (AVG), a competitive inhibitor of the enzyme ACC-synthase. AVG was applied 28 days after anthesis at 500 mg/l. This treatment resulted in a 40–50% reduction of ethylene production in the entire pod and was accompanied by a delay of pod wall senescence of approximately 4 days. Decreased endogenous ACC concentrations in both dehiscence zone and seeds of the treated pods correlated with the reduced ethylene production. In the other tissues analysed (pod wall, septum and the zone between dehiscence zone and pod wall) no such decrease in ACC concentrations or synthesis could be demonstrated. A decrease in endogenous IAA content in the dehiscence zone preceding pod opening was also observed in these experiments both in control and in AVG-treated plants.

To examine the auxin involvement in pod shattering, the synthetic auxin 4-chlorophenoxyacetic acid (4CPA) was used to manipulate auxin levels. 4CPA was applied 35 days after anthesis as a spray at 150 mg/l in order to artificially keep auxin concentration at a high level during the entire period. This resulted in a distinct retardation in pod shatter tendency (see Table 1), as well as a delay of pod wall senescence of about two weeks. No effect was observed on the endogenous phytohormone concentrations. Beta-Glucanase activity however was markedly decreased in the dehiscence zone. These results are clearly indicative of the inhibitory effect of auxins on the production and/or activity of beta-glucanase.

The decline in auxin is a major trigger of pod shatter.

TABLE 1

Force (in 10−3 N) needed to initiate and propagate pod opening as measured in the Cantilever bending test [Kadkol et al. [(1986), Aust. J. Bot. 34:595] with pods (8% moisture) of oilseed rape cv Fido. Tested plants were either untreated, sprayed with AVG to reduce ethylene values, or sprayed with 4CPA to prevent the auxin drop. (SED: Standard Error on Differences; df: degree of freedom)

|  | untreated | AVG | 4CPA | SED (27df) |
|---|---|---|---|---|
| To initiate crack | 143.6 | 170.8 | 194.9 | 14.4 |
| To propagate crack | 167.1 | 171.4 | 222.6 | 17.21 |

Demonstration of Polygalacturonate-degrading Enzyme Activity in Pod Dehiscence Zones Pods of oilseed rape cv Fido were harvested at 6.5 weeks after anthesis, stripped of the carpels and seeds, and crude enzyme extracts were prepared from tissues surrounding the dehiscence zones, including the replum with a vascular bundle and the thin membrane separating the two locules of the silique. Extracts were subsequently tested with respect to their action against polymeric substrates (uronic acids), using molecular weight down-shift assays, based on gel-permeation chromatography of substrate incubated with a boiled (used as reference) and active enzyme preparation respectively. The assay in particular detects enzymes with endo-activity as removal of single monosaccharides in an exo-fashion only changes molecular weight distribution of the polymeric substrate very slowly. Analysis for uronic acids was carried out essentially as described by Blumenkrantz and Asboe-Hansen [(1973), *Anal. Biochem.* 54: 484]. The assay was used here only to demonstrate the presence of enzyme activities in a strictly qualitative sense.

DZ preparations from oilseed rape pods contain all enzyme activities required for a full depolymerization of pectic polymers of low degree of methylation. It was found that one component of the enzyme mixture was specifically acting on polygalacturonate polymers. It was further demonstrated that only endo-polygalacturonase among known plant enzymes is responsible for the molecular weight down-shift of the polygalacturonate preparations used.

It can be concluded that endo-polygalacturonase plays an important role in the extensive degradation of middle lamella material observed during pod dehiscence.

Anatomical Observations During the Process of Dehiscence

Detailed examination of the structure of pod tissues has given more insight in the anatomical changes associated with the biochemical processes that take place in the dehiscence zone. It was observed by electron microscopy that rapid dehydration of the pod wall immediately precedes the degradation of parenchymatous cells situated in the dehiscence zone, mesocarp, septum and in the seed abcission zone. Initial signs of breakdown were shown by swelling of the cell walls. Subsequent cell-separation was seen only in the dehiscence zone, and was observed to take place along the line of the middle lamella to be followed by the dispersion of the microfibrils of the cell wall. Finally, all the cells of the dehiscence zone were observed to separate while the two valves of the pod remained attached only by the vascular strands which pass through the dehiscence zone. Analysis using electron microscopy revealed very dramatic degradation of the middle lamella during pod opening while the primary cell wall was left essentially intact but for some thinning and softening processes. These observations indicate that any processes in the primary cell wall are accessory to the degradation of the middle lamella.

The complete dissolution of the middle lamella of cells in the dehiscence zone indicates the presence of pectin degrading enzymes such as endoPG. While such enzymes degrade charged portions of the middle lamella pectins, other polysaccharide hydrolases, with affinity towards neutral polymers, are involved to complete the depolymerization of the middle lamella.

A beta-galactanase and a beta-glucanase were purified to homogeneity. Detailed investigation of the substrate specificity indicated that these enzymes are involved in thinning of the primary cell wall in the dehiscence zone.

EXAMPLE 2

Isolation of a DZ-selective Endo-polvgalacturonase cDNA Clone from *Brassica napus*

Poly-A+ mRNA of pod dehiscence zones of *Brassica napus* cv Topaz plants was prepared as follows. Twenty grams of tissue (leaves, dehiscence zones, pod walls, roots or stems) were ground in liquid nitrogen and homogenized for 30 seconds in a Waring blender with 100 ml of extraction buffer (4M guanidinium thiocyanate, 25 mM sodium citrate, pH 7.0, 0.5% sarkosyl, 0.1 M 2-mercaptoethanol). The homogenate was transferred to a fresh tube and 1/10 volume of 2M sodium acetate, pH 4.0, and 1 volume of TE saturated phenol/chloroform was added. The solution was shaked vigorously, cooled on ice for 15 min. and centrifuged at 10,000×g for 15 min at 4° C. The supernatant was re-extracted with phenol/chloroform as described above. An equal volume of isopropanol was added to the re-extracted supernatant and RNA was precipitated by an overnight incubation at −20° C. After centrifugation at 10,000×g for 15 min, the RNA pellet was dissolved in 2 ml of denaturation buffer. Fourteen ml of 4M LiCl was then added and the solution kept in an ice-bath overnight. The RNA was pelleted by centrifugation at 10,000×g for 15 min, washed in 80% ethanol, dried and dissolved in 1 ml of water. Poly-A+ RNA was isolated on an oligo-d(T) sepharose column according to the manufacturer's guidelines (Boehringer, Mannheim).

Random or oligo-d(T) primed first strand cDNA synthesis was performed using M-MLV reverse transcriptase and 6 μg of total poly-A+ RNA as prepared above according to conditions outlined by the manufacturer (Life Technologies/BRL). First strand cDNAs were used as template DNA for further PCR reactions.

Four degenerated primers were designed based on conserved regions from published polygalacturonase (PG) amino acid sequences from tomato [DellaPenna et al. (1986), *Proc. Natl. Acad. Sci. USA* 83:6420; Grierson et al. (1986), *Nucl. Acids Res.* 14: 8595], maize [Niogret et al. (1991), *Plant Mol. Biol.* 17: 1155], avocado and Oenothera [Brown and Crouch (1990), *The Plant Cell* 2: 263]. The sequences of the four primers used (PG1, PG2, PG3 and PG5) are shown in SEQ ID NoS: 2–5. A restriction enzyme site for EcoRI was introduced at the 5-end of the two upstream primers PG1 and PG3 and a BamHI site was introduced at the 5-end of the two downstream primers PG2 and PG5.

All PCR reactions had the following final composition: 50 mM KCl, 10 mM Tris-HCl, pH 8.3, 1.5 mM MgCl, and 0.001% (w/v) gelatin, 100 pmoles of degenerated primers and 1 U of Taq DNA polymerase in a 50 μl reaction volume. After an initial denaturation of template DNA at 95° C. for 3 minutes in 1×PCR reaction buffer, the PCR reaction was initiated by adding 1 U of Taq DNA polymerase in 1×PCR buffer (hot start PCR) using the following conditions: 1 min. at 95° C., 1 min. at 45° C. and 1 min. at 72° C. for 35 cycles followed by 72° C. for 3 min. For hot start nested PCR 2 1 of a PCR reaction was applied as template in a new PCR reaction. The PCR products were chloroform extracted and ethanol precipitated, redissolved in TE and digested with the restriction enzymes BamHI and EcoRI. The restricted PCR products were purified from low melting agarose, and cloned into pGEM-7z cut with BamHI and EcoRI. DNA sequences of the PCR fragments were obtained by the dideoxy chain termination method using Sequenase version 2.0 (Pharmacia).

The longest PCR fragment was obtained by using the PG1/PG5 primer combination. Hot start nested PCR was performed with the PG3/PG2, PG1/PG2 or PG3/PG5 primer combinations using a small aliquot of the PG1/PG5 PCR reaction as a template. Seven highly divergent PG-related clones were identified by sequencing of the PCR products, indicating the presence of at least seven different PG isoforms. Three forms were obtained from a single tissue only, namely lpg32-25 (SEQ ID NO:11) from dehiscence zones, kpg32-8 (SEQ ID NO:8) from pod walls and bpg32-26 (SEQ ID NO:7) from leaves. Lpg32-32 (SEQ ID NO: 12), lpg32-24 (SEQ ID NO:10) were found only in the two pod tissues, whereas lpg12-16 (SEQ ID NO:9) was obtained from all three tissues analyzed. It should be noted, that lpg35-8 (containing the DNA sequence of SEQ ID NO:1 from position 884 to 1,245) was the only type identified in the dehiscence zone when the PG3/PG5 primer combination was used in a nested PCR reaction.

The expression of the PG-related PCR clone lpg35-8 in roots, stems, leaves and hypocotyls as well as during pod development was investigated by Northern analysis as follows. Total RNA of individual tissues was separated by gel electrophoresis in 0.66 M formaldehyde/1%agarose gel [Sambrook et al. (1989), supra]. RNA was transferred onto Hybond-N filters and fixed to the filter by UV-irradiation. The filters were prehybridized for 4 hours in 5×Denhardt, 25 mM Na2HPO4, 25 mM NaH2PO4, 0.1% pyrophosphate, 750 mM NaCl, 5 mM EDTA and 100 µg/ml denatured herring sperm DNA at 68° C. The PCR products were radioactively labelled and were heat-denatured and added directly to the pre-hybridization buffer and hybridization was then continued for 16 hours at 68° C. The filter was washed according to Sambrook et al. [(1989), supra] where the final wash was carried out at 68° C. in 0.2×SSC, 0.1% SDS. The filters were autoradiographed at −80° C. using an intensifying screen.

No transcripts hybridizing to the lpg35-8 clone could be detected in total RNA isolated from roots, stems, leaves and hypocotyls. However, the lpg35-8 clone hybridized to a 1.6–1.7 kb transcript that is exclusively expressed in the dehiscence zone during all stages analyzed and was found to increase dramatically in abundance after week 5.

A DZ-selective cDNA library was constructed in Lambda ZAPS II insertion vectors (Stratagene) using 5 µg of poly-A+ RNA isolated from dehiscence zones 6 weeks after anthesis. cDNAs larger than 1 kbp were purified from a low temperature melting agarose gel and ligated into the Lambda ZAP® II vector. The primary library consisted of 1.25×10⁶ pfu with an averaged cDNA insert size of app. 1.5 kbp. Library screening was done according to standard procedures at high stringency [Sambrook et al. (1989), supra].

cDNAs were sequenced using Sequenase v. 2.0 (Amersham). Sequence analysis was performed with the GCG sequence analysis software package v. 7 [Devereux et al. (1984), Nucl. Acids Res. 12: 387].

Screening 300,000 plaques with the lpg35-8 PCR-fragment as probe gave approximately 200 positive hybridization signals. Five strongly hybridizing plaques were purified to homogeneity. After excision of the insert DNA from the lambda vector, restriction enzyme analysis showed the cDNA inserts to be approximately 1600 bp in all cDNA clones except one, which only had an insert of 1300 bp. Restriction enzyme mapping of the 4 largest cDNA inserts (designated as X, 5, 9 and 11 respectively) showed minor differences between the 4 cDNA inserts.

Most noteworthy is the presence of a NsiI restriction enzyme site in cDNA clones X and 11 and the presence of a HindII site in cDNA clone 9. In contrast, none of these restriction sites are present in CDNA clone 5. Partial sequencing of the 5' and 3' cDNA ends revealed additional sequence variations including small deletions/insertions between the different cDNA clones. These results indicate the expression in the dehiscence zone of different but highly homologous PG-encoding genes. The sequence data also showed that the larger 4 cDNA inserts all contained the complete coding sequence for the PG protein.

The complete sequence of cDNA clone X and the deduced amino acid sequence of its largest open reading frame is shown in SEQ ID NO:1. The open reading frame encodes a protein of 433 amino acids in size with an estimated molecular weight of 46.6 kD and with considerable similarity to known endopolygalacturonases. Similar to other cell wall hydrolases the presumed DZ-selective endo-PG is initially produced as a precursor containing a N-terminal signal peptide which is cleaved off co-translationally. The most likely cleavage site is located between amino acids 23 and 24 and gives rise to a mature protein with an estimated molecular weight of 44.2 kD.

Northern analysis, using cDNA clone X as a probe, confirmed and extended the previously obtained expression pattern. Total RNA was prepared as described from different tissues of the pods (the dehiscence zone, the pod walls, seeds and septum) at 5 time points (2, 3, 5, 7 and 9 weeks after anthesis—WAA). 5 µg of total RNA was seperated by gel-electrophoresis and hybridized with the radiolabelled cDNA of SEQ ID NO:1 as a probe under the stringent conditions described above. The autoradiogram was developed after overnight exposure. At 2 WAA, no signal was detectable; at 3 WAA a faint signal was observed. Based on densitometry scannings and readings, the expression level measured at time point 5 WAA was about 3.5× the amount seen at 3 WAA; at 7 WAA was about 7× the amount seen at 3 WAA; and at 9 WAA was about 12 times the amount seen at 3 WAA. No signal was detected in the pod walls or seeds. Faint expression (comparable with the level in the DZ at 3 WAA) was measured in the septum at 9 WAA.

The RNA used in this experiment has been extracted from the respective tissues of plants for which the pod development took about 9 weeks.

EXAMPLE 3
Isolation of a DZ-selective Promoter from a *B. napus* Genomic Clone Corresponding to the cDNA Clone lpq 35-8

A commercially available lambda EMBL3 *Brassica napus* cv. Bridger genomic library (Clontech Laboratories, Inc.) in *Escherichia coli* strain NM538 was screened as follows. After transfer to Hybond-N nylon membranes, the lpg35-8 cDNA was radioactively labelled using random priming, and the filters were hybridized under high stringency conditions in 5×SSPE, 5×Denhardt, 0.5% SDS, 50 µg/ml herring DNA (1×SSPE: 0.18 M NaCl, 10 mM sodium phosphate, pH 7.7, 1 mM EDTA) and washed under high stringency conditions (68° C., 0.1×SSPE, 0.1% SDS in the final wash). Approximately 600,000 plaques were screened and eleven hybridizing plaques were isolated. Two hybridizing plaques, lambda 2 and 11, were rescreened twice. Following the second rescreening phage lysates were made from lambda 2 and 11 on *E. coli* NM538 grown without maltose. DNA preparations from lambda 2 and lambda 11 were digested with SalI, subjected to gel electrophoresis and transferred to Hybond-N nylon membrane. Hybridization with the labelled lpg35-8 cDNA clone, resulted in identical hybridization patterns for both clones. A strongly hybridizing 6.3 kb SalI fragment was isolated from lambda 11 and inserted into pUC18, resulting in the master clone 6.3Sal. In order to confirm 6.3Sal as corresponding to lpg35-8, a sequencing primer was designed enabling the determination of a DNA stretch encoding two unique amino acids present in lpg35-8. Dideoxy sequencing by the Sanger method confirmed that the isolated genomic clone 6.3Sal was in this respect identical to the lpg35-8 cDNA. Restriction mapping of this clone demonstrated that it covered the entire lpg35-8 open reading frame and contained moreover app. 100 to 200 bp of downstream sequence and app. 3.5 kb of upstream sequence. The DNA sequence of a stretch of about 2.3 kb (including the promoter, the 5' untranslated region and the first 24 nucleotides of the open reading frame) was determined and is presented in SEQ ID NO:14.

In view of the fact that the cDNA clone (SEQ ID NO:1) and the genomic clone (SEQ ID NO:14) were isolated from different *B. napus* cultivars (resp. cv.Topaz and cv.Bridger), it was surprisingly found that upon alignment of both sequences the overlapping fragment displayed 100% sequence identity.

The transcription start site of the DZ selective gene corresponding to the gene contained in the 6.3Sal clone is determined using generally known techniques such as primer extension analysis [Sambrook et al. (1989) *Molecular Cloning: A Laboratory Manual,* Second Edition, Cold Spring Harbor Laboratory Press, NY] or RACE-PCR [Innis et al. (1990) *PCR Protocols: A Guide to Methods and Applications,* Academic Press Inc.]. The 5'UTL is thought to be located between positions 2,219 and 2,227 of SEQ ID NO:14.

Using well-established site-directed mutagenesis techniques [Ausubel et al. (1994), supra], the DNA sequence is modified to create a unique restriction enzyme (e.g., NcoI) recognition site around the ATG translation initiation codon of the coding sequence. This allows a straightforward fusion of the promoter region of the DZ-selective gene to a DNA sequence of interest to construct a DZ-selective chimeric gene of this invention. Using a unique restriction enzyme recognition site located between 500 to 2,000 base pairs upstream (i.e., 5') of the unique restriction site surrounding the ATG translation initiation codon, a well defined DNA fragment is isolated, that is subsequently used as a promoter cassette, hereinafter referred to as PDZ, that directs DZ-selective expression in plants.

For example, a SphI-NcoI fragment (of about 2.08 kb), which is capable of directing DZ-selective expression in plants, is then subsequently used as a promoter cassette, hereinafter referred to as PDZ1.

A DZ-selective chimeric gene (PDZ or PDZ1-gus-3'nos) is constructed comprising the following operably linked DNA fragments:

PDZ or PDZ1: the 5' regulatory region comprising a DZ-selective promoter,
gus: a DNA fragment coding for beta-glucuronidase [Jefferson et al. (1986) *Proc. Natl. Acad. Sci. USA* 83: 8447];
3'nos: the 3' untranslated end comprising the polyadenylation site of the nopaline synthase gene ("3'nos")[Depicker et al. (1982), *J. Mol. Appl. Genet.* 1: 561].

A second promoter cassette which is capable of directing DZ-selective expression in plants, was obtained using well-established site-directed mutagenesis techniques to modify the DNA sequence to create a unique restriction site immediately upstream of the ATG translation initiation codon of the coding sequence. For this purpose a SmaI site has been engineered, immediately upstream of the ATG-codon, by changing the A-nucleotides of SEQ ID NO:14 at positions 2327 and 2328 into G-nucleotides. The SphI-SmaI fragment of about 2.1 kb, hereinafter referred to as promoter cassette PDZ2, was fused at the SmaI site upstream of the GUS coding region in the plasmid pBI101 (Clontech Laboratories, Inc CA, USA), resulting in a plasmid (2.1guspgem7) carrying the chimeric PDZ2-gus-3'nos gene construct.

A chimeric selectable marker gene PSSU-bar-3'ocs was constructed [De Almeida et al. (1989), *Mol. Gen. Genet.* 218: 78]. It comprises the following operably linked DNA fragments:
PSSU: the promoter region of *Arabidopsis thaliana* ribulose-1,5-biphosphate carboxylase small subunit 1A encoding gene [Krebbers et al. (1988), *Plant Mol. Biol.* 11: 745),
bar: the region of the bar gene encoding phosphinothricin acetyl transferase[Thompson et al. (1987), *The EMBO J.* 6: 2519],
3'ocs: a 3' untranslated end comprising the polyadenylation site of the octopine synthase gene [De Greve et al. (1983), *J. Mol. Appl. Genet.* 1: 499].

Alternatively, a PSSU-bar-3'g7 was constructed comprising identical fragments as the preceeding chimeric selectable marker gene, except that the 3'ocs was replaced by the 3' untranslated end comprising the polyadenylation site of the T-DNA gene 7 (3'g7; Velten and Schell (1985), *Nucl. Acids Research,* 13, 6981).

Both the DZ-selective chimeric gene (PDZ2-gus-3'nos; cloned as a HindIII-XhoI fragment of about 4.2 kb) and the chimeric marker gene (PSSU-bar-3'g7) were introduced into the polylinker located between the border sequences of the T-DNA vector pGSV5, resulting in plasmid vector pTCO155 carrying the PDZ2-gus-3'nos and pSsuAra-bar-3'g7 chimeric gene constructs between the T-DNA border repeats. pGSV5 was derived from plasmid pGSC1700 [Cornelissen and Vandewiele (1989), *Nucl. Acids Res.* 17: 833] but differs from the latter in that it does not contain a beta-lactamase gene and that its T-DNA is characterized by the sequence of SEQ ID NO:13.

EXAMPLE 4

Construction of a Chimeric Gene Carrying the Barnase Coding Region Under Control of the Endo-PG Promoter A DZ-selective chimeric gene (PDZ-barnase-3'nos or PDZ1-barnase-3'nos or PDZ2-barnase-3'nos) is constructed comprising the following operably linked DNA fragments:
PDZ or PDZ1 or PDZ2: a 5' regulatory region of Example 3, comprising a DZ-selective promoter,
barnase: a DNA fragment coding for barnase of *Bacillus amyloliquefaciens* [Hartley (1988). *J. Mol. Biol.* 202: 913],
3'nos Both the DZ-selective chimeric gene and the PSSU-bar-3'g7or PSSU-bar-3'ocs chimeric marker genes are introduced into the polylinker located between the border sequences of the T-DNA vector pGSV5 of Example 4.

PDZ2-barnase-3'nos between T-DNA border repeats was constructed by replacing the pTA29 promoter upstream of the barnase coding region in pTC099, by the PDZ2 promoter cassette. To this end the 2.1 kb (blunted) SphI-SmaI fragment comprising PDZ2 was fused with its SmaI site to the blunted NcoI site overlapping with the ATG-codon which had been engineered at the 5' end of the coding sequence for the mature barnase in pTCO99, resulting in the plasmid vector pTPR1 carrying the PDZ2-barnase-3'nos chimeric gene between the T-DNA border repeats. The T-DNA vector part of pTC099 is derived from that of pGSV5 by insertion of an EcoRI linker (GGAATTCC) into the SmaI site of the polylinker, and a BglII linker (CAGATCTG) into the NcoI site of the polylinker followed by introduction of the chimeric pTA29barnase3'nos gene of pTCO113 [WO96/26283]

into the EcoRI site of the polylinker. Introduction of the chimeric selectable marker gene pSSUAra-bar-3'g7 in the polylinker sequence of pTPR1 between the T-DNA border repeats results in pTPR3.

An additional T-DNA vector (pTPR2) is constructed wherein the DZ-selective chimeric gene described above (PDZ2-barnase-3'nos) is accompagnied by the BglII fragment of pTCO113 [WO96/26283] comprising the barstar coding region under control of nopaline synthase promoter (pnos-barstar-3'g7) inserted into the polylinker of pTPR1 between the T-DNA border repeats. Introduction of the chimeric selectable marker gene pSSUAra-bar-3'g7 in the polylinker sequence of pTPR2 between the T-DNA border repeats results in pTPR4.

EXAMPLE 5
Construction of a DZ-selective Chimeric Gene Encoding T-DNA Gene 1 Product or the rolB Gene Product A DZ-selective chimeric gene (PDZ-g1-3'nos) is constructed comprising the following operably linked DNA fragments:

PDZ or PDZ1 orPDZ2: a 5' regulatory region of Example 3; comprising a DZ-selective promoter,
g1: a DNA fragment encoding the *Agrobacterium tumefaciens* tryptophan 2-monooxygenase (iaaM or T-DNA gene 1 product)[Gielen et al. (1984), *EMBO J.* 3: 835], obtained by polymerase chain reaction using appropriately designed primers comprising sequences respectively identical and complementary to the sequences immediately flanking gene 1.
3'nos A second DZ-selective chimeric gene (PDZ-g2-3'nos) is constructed comprising the following operably linked DNA fragments:

PDZ or PDZ1 orPDZ2: a 5' regulatory region of Example 3 comprising a DZ-selective promoter,
g2: a DNA fragment encoding the *Agrobacterium tumefaciens* indole-3-acetamide hydrolase (iaaH or T-DNA gene 2 product)[Gielen et al. (1984), *EMBO J.* 3: 835], obtained by polymerase chain reaction amplification, using appropriately designed primers comprising sequences respectively identical and complementary to the sequences immediately flanking gene 2.
3'nos Both the DZ-selective chimeric gene (either PDZ-q1-3'nos alone or in combination with PDZ-a2-3'nos) and the PSSU-bar-3'ocs or PSSU-bar-3'g7 chimeric marker gene are introduced into the polylinker located between the border sequences of the T-DNA vector pGSV5 of Example 4.

Another DZ-selective chimeric gene (PDZ-rolB-3'nos) is constructed comprising the following operably linked DNA fragments:

PDZ: the 5' regulatory region of Example 3, comprising a DZ-selective promoter,
rolB: the open reading frame of the Agrobacterium rhizogenes rolB gene [Furner et al. (1986), *Nature* 319: 422]
3'nos Both the DZ-selective chimeric gene and the PSSU-bar-3'ocs or the PSSU-bar-3'g7 chimeric marker gene are introduced into the polylinker located between the border sequences of the T-DNA vector pGSV5 of Example 4.

EXAMPLE 6
Construction of a DZ-selective Chimeric Gene Encoding a Mutant ETR1-1 Ethylene Receptor A DZ-selective chimeric gene (PDZ-etr1-1-3'nos) is constructed comprising the following operably linked DNA fragments:

PDZ or PDZ1 or PDZ2: a 5' regulatory region of Example 3, comprising a DZ-selective promoter,
etr1-1: the open reading frame of the dominant, ethylene-insensitive mutant allele of the *Arabidopsis thaliana* ETR gene [Chang et al. (1993), *Science* 262:239], isolated as a 2.7 kb fragment comprising the exons of the coding sequence separated by 5 introns obtained by PCR amplification using the plasmid carrying the 7.3 kb genomic EcoRI fragment comprising the DNA of the mutant etr1 allele [Chang et al. (1993), *Science* 262: 539] and appropriately designed primers.
3'nos Both the DZ-selective chimeric gene and the PSSU-bar-3'ocs or PSSU-bar-3'g7 chimeric marker gene are introduced into the polylinker located between the border sequences of the T-DNA vector pGSV5 of Example 4.

EXAMPLE 7
Construction of a DZ-selective Chimeric Gene Encoding Antisense RNA Complementary to mRNA from which the cDNA of SEQ ID No:1 can be Prepared A DZ-selective chimeric gene (PDZ-anti-PG-1-3'nos) was constructed comprising the following operably linked DNA fragments:

PDZ or PDZ1 or PDZ2: a 5' regulatory region of Example 3, comprising a DZ-selective promoter,
anti-PG-1: a DNA fragment encoding an RNA which is complementary to the RNA encoded by the region of SEQ ID NO:1 between nucleotide positions 10 and 1600.
3'nos To this end the CaMV35S promoter of the 35S-antisense PG construct comprising a DNA sequence complementary to the complete sequence of SEQ ID NO:1 cloned between a CaMV 35S promoter and a polyadenylation signal (as described below) was eliminated by digetion with HincII and XhoI, and replaced by the fragment comprising PDZ2.

Both the DZ-selective chimeric gene and the PSSU-bar-3'g7 or PSSU-bar-3'ocs chimeric marker genes are introduced into the polylinker located between the border sequences of the T-DNA vector pGSV5 of Example 4.

Another DZ-selective chimeric gene (PDZ-anti-PG-2-3'nos) is constructed comprising the following operably linked DNA fragments:

PDZ or PDZ1 or PDZ2: a 5' regulatory region of Example 3, comprising a DZ-selective promoter,
anti-PG-2: a DNA fragment encoding an RNA which is complementary to the RNA encoded by the region of SEQ ID NO:1 between nucleotide positions 20 and 700.
3'nos Both the DZ-selective chimeric gene and the PSSU-bar-3'ocs or the PSSU-bar-3'g7 chimeric marker gene are introduced into the polylinker located between the border sequences of the T-DNA vector pGSV5 of Example 4.

Still another DZ-selective chimeric gene (PDZ-anti-PG-3-3'nos) is constructed comprising the following operably linked DNA fragments:

PDZ or PDZ1 or PDZ2: the 5' regulatory region of Example 3, comprising a DZ-selective promoter,
anti-PG-3: a DNA fragment encoding an RNA which is complementary to the RNA encoded by the region of SEQ ID NO:1 between nucleotide positions 800 and 1600.
3'nos Both the DZ-selective chimeric gene and the PSSU-bar-3'ocs or the PSSU-bar-3'g7 chimeric marker gene are introduced into the polylinker located between the border sequences of the T-DNA vector pGSV5 of Example 4.

Three other antisense constructs were constructed comprising a CaMV 35S promoter, a DNA sequence complementary to the complete sequence of SEQ ID NO:1, or a DNA sequence complementary to 679 bp of the 3' end of SEQ ID NO:1 (A67), or a DNA sequence complementary to 336 bp of the 3' end of SEQ ID NO:1 (A30), and a polyadenylation signal. The CDNA of cDNA-library clone X was excised as a EcoRI-XhoI fragment and inserted in pBluescript® (Stratagene, CA USA). The full length cDNA was isolated as a BamHI-XhoI fragment from this plasmid and inserted into BamHI-XhoI digested pRT100 vector [Topfer et al (1987) *Nucleic Acids Research* 15, 5890], between the CaMV35S promoter and polyadenylation signal. The resulting plasmid was digested with BamHI and EcoRI, treated with Klenow polymerase and self-ligated.

The HaeIII-XhoI fragment of the pBluescript® plasmid with the cDNA insert comprising the 3' end 679 bp of SEQ ID NO:1 was inserted into the SmaI-XhoI digested pRT100 vector, between the CaMV35S promoter and polyadenylation signal, resulting in plasmid A67.

The A 67 construct was digested with XbaI and StyI, treated with Klenow polymerase and self-ligated, resulting in plasmid A30, comprising the DNA sequence complementary to 336 bp of the 3' end of SEQ ID NO:1 between the CaMV35S promoter and polyadenylation signal. The chimeric genes were isolated as PstI fragments.

35S-antisense-PG chimeric genes and the PSSU-bar-3'ocs or the PSSU-bar-3'g7 chimeric marker gene are introduced into the polylinker located between the border sequences of the T-DNA vector pGSV5 of Example 4.

EXAMPLE 8
Transformation of Oilseed Rape and Characterization of the Transformants
Agrobacterium-mediated Transformation Hypocotyl explants of *Brassica napus* are obtained, cultured and transformed essentially as described by De Block et al. [(1989), *Plant Physiol.* 91: 694), except for the following modifications:

hypocotyl explants are precultured for 3 days in A2 medium [MS, 0.5 g/l Mes (pH5.7), 1.2% glucose, 0.5% agarose, 1 mg/l 2,4-D, 0.25 mg/l naphthalene acetic acid (NAA)and 1 mg/l 6-benzylaminopurine (BAP)].

infection medium A3 is MS, 0.5 g/l Mes (pH5.7), 1.2% glucose, 0.1 mg/l NAA, 0.75 mg/l BAP and 0.01 mg/l gibberellinic acid (GA3).

selection medium A5 is MS, 0.5 g/l Mes (pH5.7), 1.2% glucose, 40 mg/l adenine.$SO_4$, 0.5 g/l polyvinylpyrrolidone (PVP), 0.5% agarose, 0.1 mg/l NAA, 0.75 mg/l BAP, 0.01 mg/l GA3, 250 mg/l carbenicillin, 250 mg/l triacillin, 0.5 mg/l $AgNO_3$.

regeneration medium A6 is MS, 0.5 g/l Mes (pH5.7), 2% sucrose, 40 mg/l adenine.$SO_4$, 0.5 g/l PVP, 0.5% agarose, 0.0025 mg/l BAP and 250 mg/l triacillin.

healthy shoots are transferred to rooting medium which was A8: 100–130 ml half concentrated MS, 1% sucrose (pH5.0), 1 mg/l isobutyric acid (IBA), 100 mg/l triacillin added to 300 ml perlite (final pH6.2) in 1 liter vessels.

MS stands for Murashige and Skoog medium [Murashige and Skoog (1962), *Physiol. Plant.* 15: 473).

Hypocotyl explants are infected with *Agrobactelium tumefaciens* strain C58C1RifR carrying:

a helper Ti-plasmid such as pGV4000 which is a derivative of pMP90 [Koncz and Schell (1986), *Mol. Gen. Genet.* 204: 383) obtained by insertion of a bacterial chloramphenicol resistance gene linked to a 2.5 kb fragment having homology with the T-DNA vector pGSV5, into pMP90.

T-DNA vector derived from pGSV5 comprising between the T-DNA borders the DZ-selective chimeric gene of Example 3, 4, 5, 6, or 7 and the chimeric marker gene.

Selected lines from these transformants harboring one type of the chimeric genes of the invention are further used for crossing experiments, yielding new lines comprising combinations of the chimeric genes of the invention.
Characterization of Transformants Transformed *Brassica napus* plants of Example 8, comprising in their nuclear genomes the DZ-selective chimeric gene of Example 3, were in various tissues of the plants using conventional in-situ histochemical techniques [De Block and Debrouwer (1992), *The Plant Journal* 2:261; De Block and Debrouwer (1993), *Planta* 189: 218]. High GUS activity was found in the DZ layer of the pods, as reflected by the strong staining, while no background labelling was observed in other pod tissues, attesting to the fact that the promoter of Example 3 directs expression selectively in the pod DZ.

Transformed *Brassica napus* plants of Example 8, comprising in their nuclear genomes the DZ-selective chimeric genes of Example 4, 5, 6 or 7 alone or in combination are characterized with respect to the following characteristics:

1) changes in physiological processes by analysing diminution of expression of targetted gene products (such as cell wall hydrolases) or diminution in the biochemical activities (See Blumenkratz, supra), by monitoring the heterologous gene expression (See, Sambrook et al supra), or by measuring the endogenous levels of IAA and IAA conjugates during development (See, Example 1)

2) changes in DZ anatomy and DZ cell walls during pod senescence by light microscopy and transmission electron microscopy; the extent of cell separation after pod opening by analysing seperated DZ surfaces with the scanning electron microscope (See, Example 1)

3) changes in the mechanical properties of the DZ and their seed shatter resistance by analysing the shatter resistance of individual pods. This can be done by the cantilever test as described by Kadkol et al. [(1986), *Aust. J. Bot.* 34: 595]. Clamped pods are loaded as a cantilever in a "universal testing machine", consisting of a cross-head beam moved by actuators to which a load cell applies a constant force to deflect the pod. This records the displacement and the force necessary to initiate and propagate an opening in the pod dehiscence zone. Alternatively, a first assessment of shatter susceptibility is carried out with detached pods subjected to controlled vibration (simulating impact with the canopy and machinery). The vibration consists of horizontal oscillation of fixed amplitude in a container with steel balls to enhance energy transfer. In yet another procedure, susceptibility to crack propagation is determined by friction measurement. In this case, the force generated due to friction between a wedge forced along the DZ is recorded and enables comparison of DZ tissues in selected, extreme examples of resistance.

Finally, individual selected lines are subjected to per se performance analysis in the field. The design of these field trials is based on the cultivation of individual lines (homozygous for the transgene) at two locations in three replicates.

Analysis of a statistically significant number of pods from different transformed plants demonstrates an increase in pod shatter resistance when compared to untransformed control plants.

Needless to say, the use of the DZ-selective promoter and recombinant DNA constructs of this invention is not limited to the transformation of the specific plant of the examples. Such promoter and recombinant DNA constructs can be useful in transforming any crop, where the promoter can drive gene expression, preferably where such expression is to occur abundantly in the plant cells of the dehiscence zone.

Also, the use of the DZ-selective promoter of the present invention is not limited to the control of particular transcribed DNA regions of the invention, but can be used to control expression of any foreign gene or DNA fragment in a plant.

Furthermore, the present invention is not limited to the specific DZ-selective promoter described in the above Examples. Rather, the present invention encompasses promoters, equivalent to the one of the Examples, which can be used to control the expression of a structural gene, at least substantially selectively in the plant cells of the dehiscence zone. Indeed, the DNA sequence of the DZ-selective promoter of the Examples can be modified by replacing some of its nucleotides with other nucleotides and/or deleting or inserting some nucleotides, provided that such modifications do not alter substantially the timing, level and tissue-specificity of expression controlled by the promoter, as measured by GUS assays in transgenic plants transformed with a chimeric gus gene under control of the modified promoter (see, Example 3). Up to 20% of the nucleotides of a promoter may be changed without affecting the characteristics of the promoter. Such promoters can be isolated by hybridization under standard conditions (Sambrook et al,supra) using selected DNA fragments of SEQ ID NO:14, as described above.

All publications (including patent publications) cited in this application are hereby incorporated by reference.

What is claimed is:

1. An isolated DNA sequence having promoter activity, wherein the DNA sequence comprises at least the nucleotide sequence of SEQ ID NO:14 from the nucleotide at position 1,839 to the nucleotide at position 2,328.

2. The DNA of claim 1, which comprises at least the nucleotide sequence of SEQ ID NO: 14 starting between a SphI and BamHI site and ending at the nucleotide at position 2,328.

3. The DNA of claim 2, which comprises at least the nucleotide sequence of SEQ ID NO:14 from the nucleotide at position 1 to the nucleotide at position 2,328.

4. A chimeric DNA construct comprising the following operably linked elements:

a. the DNA sequence of anyone of claims 1 to 3; and b. a nucleotide sequence encoding barnase.

5. A Brassica plant cell or plant cell culture thereof, each transformed with the chimeric DNA construct of claim 4.

6. A seed of a Brassica plant containing the chimeric DNA construct of claim 4.

7. The plant cell or plant cell culture of claim 5, wherein each of said plant cell or plant culture further comprises a second chimeric DNA construct, said second DNA construct comprising a plant-expressible promoter operably linked to a DNA encoding barstar.

8. The seed of claim 6, which further comprises a second chimeric DNA construct, said second DNA construct comprising a plant-expressible promoter operably linked to a DNA encoding barstar.

9. A transformed plant obtained from any one of claim 5, 6, 7, or 8.

10. A Brassica plant comprising the chimeric DNA of claim 4.

11. The Brassica plant according to claim 10, further comprising a second DNA construct comprising a plant-expressible promoter operably linked to a DNA encoding barstar.

* * * * *

SEQUENCE LISTING

```
<160> NUMBER OF SEQ ID NOS:  14

<210> SEQ ID NO 1
<211> LENGTH: 1631
<212> TYPE: DNA
<213> ORGANISM: Brassica napus
<220> FEATURE:
<223> OTHER INFORMATION: Location 95-163 = region encoding the presumed
      endo-PG signal peptide.
<223> OTHER INFORMATION: Location 884-900 = region of the endo-PG cDNA
      corresponding to oligonucleotide PG3
<223> OTHER INFORMATION: Location 1059-1073 = region of the endo-PG cDNA
      complementary to oligonucleotide PG2
<223> OTHER INFORMATION: Location 1229-1245 = region of the endo-PG cDNA
      complementary to oligonucleotide PG5
<221> NAME/KEY: CDS
<222> LOCATION: (95)..(1393)
<223> OTHER INFORMATION: Location 821-837 = region of endo-PG cDNA
      corresponding to oligonucleotide PG1.
<223> OTHER INFORMATION: Strain cv. Topaz.
<221> NAME/KEY: unsure
<222> LOCATION: (1439)
<223> OTHER INFORMATION: n = a, c, g, t, any, other, unknown, or other

<400> SEQUENCE: 1
ggcacgagaa aaactgcaaa gagtctcata ttagttctta ctctcaagaa tcaaacacac        60
tctttctaaa aagattagcg tttcaaaccc cgaa atg gcc cgt tgt ttt gga agt      115
                                     Met Ala Arg Cys Phe Gly Ser
                                      1               5 cta gct gtt ttc tta tgc gtt ctt ttg atg ctc gct tgc tgc caa gct        163
Leu Ala Val Phe Leu Cys Val Leu Leu Met Leu Ala Cys Cys Gln Ala
         10                  15                  20 ttg agt agc aac gta gat gat gga tat ggt cat gaa gat gga agc ttc        211
Leu Ser Ser Asn Val Asp Asp Gly Tyr Gly His Glu Asp Gly Ser Phe
 25                  30                  35 gaa tcc gat agt tta atc aag ctc aac aac gac gac gac gtt ctt acc        259
Glu Ser Asp Ser Leu Ile Lys Leu Asn Asn Asp Asp Asp Val Leu Thr
 40                  45                  50                  55 ttg aaa agc tct gat aga ccc act acc gaa tca tca act gtt agt gtt        307
Leu Lys Ser Ser Asp Arg Pro Thr Thr Glu Ser Ser Thr Val Ser Val
                 60                  65                  70 tcg aac ttc gga gcc aaa gga gat gga aaa acc gat gat act cag gct        355
Ser Asn Phe Gly Ala Lys Gly Asp Gly Lys Thr Asp Asp Thr Gln Ala
             75                  80                  85 ttc aag aaa gca tgg aag aag gca tgt tca aca aat gga gtt act act        403
Phe Lys Lys Ala Trp Lys Lys Ala Cys Ser Thr Asn Gly Val Thr Thr
         90                  95                 100
```

```
ttc tta att cct aaa gga aag act tat ctc ctt aag tct att aga ttc      451
Phe Leu Ile Pro Lys Gly Lys Thr Tyr Leu Leu Lys Ser Ile Arg Phe
    105                 110                 115 aga ggc cca tgc aaa tct tta cgt agc ttc cag atc cta ggc act tta      499
Arg Gly Pro Cys Lys Ser Leu Arg Ser Phe Gln Ile Leu Gly Thr Leu
120                 125                 130                 135 tca gct tct aca aaa cga tcg gat tac agt aat gac aag aac cac tgg      547
Ser Ala Ser Thr Lys Arg Ser Asp Tyr Ser Asn Asp Lys Asn His Trp
                140                 145                 150 ctt att ttg gaa gac gtt aat aat cta tca atc gat ggc ggc tcg gcg      595
Leu Ile Leu Glu Asp Val Asn Asn Leu Ser Ile Asp Gly Gly Ser Ala
                155                 160                 165 ggg att gtt gat ggc aac gga aat atc tgg tgg caa aac tca tgc aaa      643
Gly Ile Val Asp Gly Asn Gly Asn Ile Trp Trp Gln Asn Ser Cys Lys
        170                 175                 180 atc gac aaa tct aag cca tgc aca aaa gcg cca acg gct ctt act ctc      691
Ile Asp Lys Ser Lys Pro Cys Thr Lys Ala Pro Thr Ala Leu Thr Leu
185                 190                 195 tac aac cta aag aat ttg aat gtg aag aat ctg aga gtg aga aat gca      739
Tyr Asn Leu Lys Asn Leu Asn Val Lys Asn Leu Arg Val Arg Asn Ala
200                 205                 210                 215 cag cag att cag att tcg att gag aaa tgc aac aat gtt ggc gtt aag      787
Gln Gln Ile Gln Ile Ser Ile Glu Lys Cys Asn Asn Val Gly Val Lys
                220                 225                 230 aat gtt aag atc act gct cct ggc gat agt ccc aac acg gat ggt att      835
Asn Val Lys Ile Thr Ala Pro Gly Asp Ser Pro Asn Thr Asp Gly Ile
            235                 240                 245 cat atc gtt gct act aaa aac att cga atc tcc aat tca gac att ggg      883
His Ile Val Ala Thr Lys Asn Ile Arg Ile Ser Asn Ser Asp Ile Gly
        250                 255                 260 aca ggt gat gat tgt ata tcc att gag gat gga tcg caa aat gtt caa      931
Thr Gly Asp Asp Cys Ile Ser Ile Glu Asp Gly Ser Gln Asn Val Gln
265                 270                 275 atc aat gat tta act tgc ggc ccc ggt cat ggg atc agc att gga agc      979
Ile Asn Asp Leu Thr Cys Gly Pro Gly His Gly Ile Ser Ile Gly Ser
280                 285                 290                 295 ttg ggg gat gac aat tcc aaa gct tat gta tcg gga att gat gtg gat     1027
Leu Gly Asp Asp Asn Ser Lys Ala Tyr Val Ser Gly Ile Asp Val Asp
                300                 305                 310 ggt gct acg ctc tct gag act gac aat gga gta aga atc aag act tac     1075
Gly Ala Thr Leu Ser Glu Thr Asp Asn Gly Val Arg Ile Lys Thr Tyr
            315                 320                 325 cag gga ggg tca gga act gct aag aac att aaa ttc caa aac att cgt     1123
Gln Gly Gly Ser Gly Thr Ala Lys Asn Ile Lys Phe Gln Asn Ile Arg
        330                 335                 340 atg gat aat gtc aag aat ccg atc ata atc gac cag aac tac tgc gac     1171
Met Asp Asn Val Lys Asn Pro Ile Ile Ile Asp Gln Asn Tyr Cys Asp
345                 350                 355 aag gac aaa tgc gaa cag caa gaa tct gcg gtt caa gtg aac aat gtc     1219
Lys Asp Lys Cys Glu Gln Gln Glu Ser Ala Val Gln Val Asn Asn Val
360                 365                 370                 375 gtg tat cag aac ata aaa ggt acg agc gca aca gat gtg gcg ata atg     1267
Val Tyr Gln Asn Ile Lys Gly Thr Ser Ala Thr Asp Val Ala Ile Met
                380                 385                 390 ttt aat tgc agt gtg aaa tat cca tgc caa ggt att gtg ctt gag aat     1315
Phe Asn Cys Ser Val Lys Tyr Pro Cys Gln Gly Ile Val Leu Glu Asn
            395                 400                 405 gtg aac atc aaa gga gga aaa gct tct tgc gaa aat gtc aat gtt aag     1363
Val Asn Ile Lys Gly Gly Lys Ala Ser Cys Glu Asn Val Asn Val Lys
        410                 415                 420
```

```
gat aaa ggc act gtt tct cct aaa tgc cct taattactaa gctgattatg   1413
Asp Lys Gly Thr Val Ser Pro Lys Cys Pro
    425                 430 taatatacat aaatacgtag tatatntaat tatagatgca tgtatatcgt tatctacgta   1473
ttgattcttg atatatatag aaaactaaag atatatggga atatacatac aatagttgag   1533
ataattgttg tcttgtatat gattcactga agttgattgc ttgtccatga ataaatgaat   1593
aatatcattt ctctaaaaaa aaaaaaaaaa aaaaaaaa   1631

<210> SEQ ID NO 2
<211> LENGTH: 433
<212> TYPE: PRT
<213> ORGANISM: Brassica napus
<220> FEATURE:
<223> OTHER INFORMATION: Strain cv. Topaz.

<400> SEQUENCE: 2
```

Met Ala Arg Cys Phe Gly Ser Leu Ala Val Phe Leu Cys Val Leu Leu
 1               5                  10                  15

Met Leu Ala Cys Cys Gln Ala Leu Ser Ser Asn Val Asp Asp Gly Tyr
            20                  25                  30

Gly His Glu Asp Gly Ser Phe Glu Ser Asp Ser Leu Ile Lys Leu Asn
        35                  40                  45

Asn Asp Asp Asp Val Leu Thr Leu Lys Ser Ser Asp Arg Pro Thr Thr
    50                  55                  60

Glu Ser Ser Thr Val Ser Val Ser Asn Phe Gly Ala Lys Gly Asp Gly
65                  70                  75                  80

Lys Thr Asp Asp Thr Gln Ala Phe Lys Lys Ala Trp Lys Lys Ala Cys
                85                  90                  95

Ser Thr Asn Gly Val Thr Thr Phe Leu Ile Pro Lys Gly Lys Thr Tyr
            100                 105                 110

Leu Leu Lys Ser Ile Arg Phe Arg Gly Pro Cys Lys Ser Leu Arg Ser
        115                 120                 125

Phe Gln Ile Leu Gly Thr Leu Ser Ala Ser Thr Lys Arg Ser Asp Tyr
    130                 135                 140

Ser Asn Asp Lys Asn His Trp Leu Ile Leu Glu Asp Val Asn Asn Leu
145                 150                 155                 160

Ser Ile Asp Gly Gly Ser Ala Gly Ile Val Asp Gly Asn Gly Asn Ile
                165                 170                 175

Trp Trp Gln Asn Ser Cys Lys Ile Asp Lys Ser Lys Pro Cys Thr Lys
            180                 185                 190

Ala Pro Thr Ala Leu Thr Leu Tyr Asn Leu Lys Asn Leu Asn Val Lys
        195                 200                 205

Asn Leu Arg Val Arg Asn Ala Gln Gln Ile Gln Ile Ser Ile Glu Lys
    210                 215                 220

Cys Asn Asn Val Gly Val Lys Asn Val Lys Ile Thr Ala Pro Gly Asp
225                 230                 235                 240

Ser Pro Asn Thr Asp Gly Ile His Ile Val Ala Thr Lys Asn Ile Arg
                245                 250                 255

Ile Ser Asn Ser Asp Ile Gly Thr Gly Asp Asp Cys Ile Ser Ile Glu
            260                 265                 270

Asp Gly Ser Gln Asn Val Gln Ile Asn Asp Leu Thr Cys Gly Pro Gly
        275                 280                 285

His Gly Ile Ser Ile Gly Ser Leu Gly Asp Asp Asn Ser Lys Ala Tyr
    290                 295                 300

Val Ser Gly Ile Asp Val Asp Gly Ala Thr Leu Ser Glu Thr Asp Asn
305                 310                 315                 320

Gly Val Arg Ile Lys Thr Tyr Gln Gly Gly Ser Gly Thr Ala Lys Asn
                325                 330                 335

Ile Lys Phe Gln Asn Ile Arg Met Asp Asn Val Lys Asn Pro Ile Ile
            340                 345                 350

Ile Asp Gln Asn Tyr Cys Asp Lys Asp Lys Cys Glu Gln Gln Glu Ser
                355                 360                 365

Ala Val Gln Val Asn Asn Val Val Tyr Gln Asn Ile Lys Gly Thr Ser
        370                 375                 380

Ala Thr Asp Val Ala Ile Met Phe Asn Cys Ser Val Lys Tyr Pro Cys
385                 390                 395                 400

Gln Gly Ile Val Leu Glu Asn Val Asn Ile Lys Gly Gly Lys Ala Ser
                405                 410                 415

Cys Glu Asn Val Asn Val Lys Asp Lys Gly Thr Val Ser Pro Lys Cys
                420                 425                 430

Pro

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      oligonucleotide PG1
<221> NAME/KEY: modified_base
<222> LOCATION: (16)
<223> OTHER INFORMATION: i
<223> OTHER INFORMATION: Location 22 and Location 25 =  n = unknown.

<400> SEQUENCE: 3
ccaggaattc aayacngayg gnrtnca                                          27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      oligonucleotide PG2
<221> NAME/KEY: modified_base
<222> LOCATION: (12)
<223> OTHER INFORMATION: i
<221> NAME/KEY: unsure
<222> LOCATION: ()..()
<223> OTHER INFORMATION: Location 21 and Location 24 = n = a, c, g, t,
      any, unknown, or other.

<400> SEQUENCE: 4
cgacggatcc angtyttdat nckna                                            25

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      oligonucleotide PG3
<221> NAME/KEY: unsure
<222> LOCATION: ()..()
<223> OTHER INFORMATION: any n = a, c, g, t, any, unknown, or other

<400> SEQUENCE: 5
ggacgaattc acnggngayg aytgyat                                          27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      oligonucleotide PG5
<221> NAME/KEY: modified_base
<222> LOCATION: (13)
<223> OTHER INFORMATION: i
<221> NAME/KEY: modified_base
<222> LOCATION: (16)
<223> OTHER INFORMATION: i
<221> NAME/KEY: modified_base
<222> LOCATION: (19)
<223> OTHER INFORMATION: i

<400> SEQUENCE: 6
cacaggatcc swngtnccny kdatrtt                                      27

<210> SEQ ID NO 7
<211> LENGTH: 155
<212> TYPE: DNA
<213> ORGANISM: Brassica napus
<220> FEATURE:
<223> OTHER INFORMATION: PCR fragment BPG32-26 from first strand cDNA.
      Strain cv. Topaz
<221> NAME/KEY: unsure
<222> LOCATION: (13)..(19)
<223> OTHER INFORMATION: any n = a, c, g, t, any, unknown, or other

<400> SEQUENCE: 7
tcgattcaaa ccggttgctc caatgtgtat gttcacaatg tgaattgtgg accaggacat     60
ggcatcagca tagggagtct tggtaaagac agtaccaaag cttgtgtctc caatataaca    120
gtcagagatg tagttatgca caacacaatg actgg                               155

<210> SEQ ID NO 8
<211> LENGTH: 155
<212> TYPE: DNA
<213> ORGANISM: Brassica napus
<220> FEATURE:
<223> OTHER INFORMATION: PCR fragment KPG32-8 from first strand cDNA.
      Strain cv. Topaz.

<400> SEQUENCE: 8
tctattggag acgggacgag agaccttctt gtcgaaagag ttacatgcgg tccgggacat     60
ggaatcagta ttggaagcct cggtttatac gtgaaggagg aagacgtcac tggcatcagg    120
gtcgtgaact gcaccctcat aaacactgac aatgg                               155

<210> SEQ ID NO 9
<211> LENGTH: 219
<212> TYPE: DNA
<213> ORGANISM: Brassica napus
<220> FEATURE:
<223> OTHER INFORMATION: PCR fragment LPG12-16 from first strand cDNA.
      Strain cv. Topaz.

<400> SEQUENCE: 9
tttgggaaga agtgacggag tcaagatcct taacacattc atctccaccg gagacgactg     60
tatctccgtt ggagatggga tgaagaacct tcacgtggag aaagtcacct gcggtccagg    120
acatggaatc agtgtcggaa gccttggaag gtacggaaac gaacaggatg tcagcggcat    180
tagagtcata aactgcactc tccaacagac tgacaacgg                           219

<210> SEQ ID NO 10
<211> LENGTH: 155
<212> TYPE: DNA
<213> ORGANISM: Brassica napus
<220> FEATURE:
<223> OTHER INFORMATION: PCR fragment LPG32-24 from first strand cDNA.
      Strain cv. Topaz.

<400> SEQUENCE: 10
tccattggag gcggtactga aaatttactt gtcgagggcg tagaatgtgg accaggacac      60
ggtctttcca tcggaagtct tggaaagtac cctaatgagc aaccagtgaa aggaatcacc     120
attcgtaaat gcatcatcaa gcataccgat aatgg                                155

<210> SEQ ID NO 11
<211> LENGTH: 155
<212> TYPE: DNA
<213> ORGANISM: Brassica napus
<220> FEATURE:
<223> OTHER INFORMATION: PCR fragment LPG32-25 from first strand cDNA.
      Strain cv. Topaz.

<400> SEQUENCE: 11
tctgttgggg acgggatgaa aaaccttctt gtcgaaagag tttcatgcgg tccgggacac      60
ggaatcagta ttggaagcct cggattatac gggcacgagg aagacgtcac tggcgtcaag     120
gtcgtgaact gcaccctcag aaatactgac aatgg                                155

<210> SEQ ID NO 12
<211> LENGTH: 155
<212> TYPE: DNA
<213> ORGANISM: Brassica napus
<220> FEATURE:
<223> OTHER INFORMATION: PCR fragment LPG32-32 from first strand cDNA.
      Strain cv. Topaz.

<400> SEQUENCE: 12
tccgtgggag atgggatgaa gaatctcctc attgagaaag ttgtgtgcgg tccaggacac      60
ggaatcagtg ttggaagcct tggaaggtac ggatgggagc aagatgtcac tgacattaac     120
gttaagaact gtaccctcga gggaaccgac aacgg                                155

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence:DNA sequence
      of the T-DNA of pGSV5
<223> OTHER INFORMATION: Location 1-25 = right border (RB) sequence from
      the T-DNA of pGSV5.
<223> OTHER INFORMATION: Location 26-75 = multiple cloning site (MCS).
<223> OTHER INFORMATION: Location 76-100 = left border (LB) sequence
      from the T-DNA of pGSV5.

<400> SEQUENCE: 13
aattacaacg gtatatatcc tgccagtact cggccgtcga ccgcggtacc cggggaagct      60
tagatccatg gagccattta caattgaata tatcctgccg                           100

<210> SEQ ID NO 14
<211> LENGTH: 2352
<212> TYPE: DNA
<213> ORGANISM: Brassica napus
<220> FEATURE:
<223> OTHER INFORMATION: Location 2329-2331 = translation initiation
      codon.

<223> OTHER INFORMATION: Location 246-251 = SphI restriction enzyme
     recognition site.
<223> OTHER INFORMATION: Location 2219-2227 = transcript_star = region
     containing the putative location of transcription
     start site.
<223> OTHER INFORMATION: Strain cv. Bridger.
<223> OTHER INFORMATION: Location 1836-1841 = HindII restriction enxyme
     recognition site.
<223> OTHER INFORMATION: Location 2327-2332 = sequence mutated to form a
     NcoI restriction enzyme recognition site (AAATGG
     changed to CCATGG).

<400> SEQUENCE: 14

```
acgagaatcg agagaaacaa aaactctcgt cgcaagcaca agtttggggt aggttgtatg     60
gtgtaagaat gacgggccat agagaataat gtcttccact cttgccaaac ggactgaaac    120
catcagtaca taatccaagg tagacatttc ttctctcata cgcaaagtcg ggatactttg    180
attggaaatg cttccacgct tttgcatctg aaggatgtct gatctcacca tctgttgagt    240
gctccgcatg ccatctcatt ggttgcgctg tgcgttcaga cagatacaac ctctgcaacc    300
tttccgtcaa aggtaaatac cacatccttt tatatggcac tggaactctt ccactcgtat    360
ctttataacg aggctttcca caaaatttgc atgtaacccg ctgttcatcc gccctccaat    420
aaatcatgca gttgtcgctg catacatcta ttacctgata cgccaagacc agctacgagt    480
ttctgaacct cgtagtatga accaggagct acattattct cgggtagaat acctttttaca  540
aaatcagcaa tcgcatccac acagtcttca gccaaattat aatcttttc aatgcccatc    600
aatcttgtag cagatgataa agctgaatga ccatctctgc aaccttcgta caatggttgc    660
tttccagcat ccaacatatc ataaaatttc ctagcttgtg cattgggtaa atcttcccct    720
ctaaaatgat catttaccat ctgctcagta cctacaccat aatctacatc cgttctaatt    780
ggttcttcta atctaaccgc tggctgaggt tcgctagtac taccatgttc ataatcagtt    840
tccccatgat gataccaaat tttgtaactt cgtgtaaacc cactcaaata tagatgagtc    900
caaacatccc actctttaat aacttttcta tttttacaat tagagcaaga acatcttaac    960
atacatgttt ttgcttccgg ttgtcggtga actaacccca tgaattcggt tatacctcgt   1020
tggtattctt ccgtaagcaa tctcgtgttc ggatccaaat gaggtcgatc gatccaagaa   1080
cgaaaataat ttgaagaaga catattttt atgaatcaaa ttcgtgtgta aatagagtaa    1140
gagggaggat gaagatatgg agtgaatgaa gaggaagagg agtgcttgta tttatagttt   1200
aaatcctgcc gacagaccga ggaaattccg acggaattcc gacggaaaag gctagttcgt   1260
cggaatttcc tcggaatttt gtaaaatccc ccagcggctc tccaacggct ataatatttc   1320
ctcggaattc atcggtttt tccgaggaac acatttttcc tcggaatttc tcggaatat    1380
tccaacggat tgatatttcc tcggaattcc gtcggtatat tccaaggaaa cccaattttg   1440
tgtttcctca gaatttcctc agaaattcct cgggatattc cgaggatttc attttccgtc   1500
ggaatgtcca tcagaatacc gctgtttttct tgtagtgatt attatttttt ttttcagata  1560
aaaaaaaag aaatatcaac caatcgctga ctgtcacata ttgtgggggc ccacaaatag   1620
tgcaaggact cactaagaaa aagttttat tttagaattt tagtaattga attcttaact    1680
tttggtggag ttcactgatt atttaattat tttttttaa gaactcaccc ttaagaattg   1740
ttgttgcgga tgttctaata tcagcatcac acaccaaaat aaaaagcacg aaagagtaaa   1800
agggacccaa cactactatc gaactttgaa agacggttga cgccgacgtt tatcactttt   1860
gcttatatgt tttcaacttt ttatatctaa tgtagggata tatacatcac gtaatgttag   1920
ctcagtaatt gcacatgatg gaatgttact gtgaatggta tacgatgatg aatataaact   1980
```

```
ctttctagt agaaaataac taactaatta aactctctat caatcaagaa agcaataaaa    2040
atcaataaaa agataaatta aaatggaggg gagaggagat aaaggttaga agctagggtg    2100
tgatgttttc gtatcaatct caatctctct ccatacctcc aacgccatta atacttgaat    2160
aaacatataa aatttctcca ttgaattgcc tataaataca catacatccc acttcttcaa    2220
tttcatatta caaaagcctc ccaaaaactg caaagagtct catattagtt cttactctca    2280
agaatcaaac acactctttc taaaaagatt agcgtttcaa accccgaaat ggcccgttgt    2340
tttggaagtc ta                                                        2352
```